United States Patent
Hicks et al.

(10) Patent No.: US 10,897,877 B2
(45) Date of Patent: Jan. 26, 2021

(54) FOOD SUPPLY TRACKING, AUTHENTICATION, AND FEEDBACK SYSTEM

(71) Applicant: HERDX, INC., Boerne, TX (US)

(72) Inventors: Ronald B. Hicks, Boerne, TX (US); Sarah C. Harkleroad, San Antonio, TX (US); Austin Adams, Boerne, TX (US); David Schroeder, Boerne, TX (US)

(73) Assignee: HerdX, Inc., Boerne, TX (US)

( * ) Notice: Subject to any disclaimer, the term of this patent is extended or adjusted under 35 U.S.C. 154(b) by 0 days.

(21) Appl. No.: 16/404,719

(22) Filed: May 6, 2019

(65) Prior Publication Data

US 2019/0335715 A1 Nov. 7, 2019

Related U.S. Application Data

(60) Provisional application No. 62/666,985, filed on May 4, 2018.

(51) Int. Cl.
*A01K 29/00* (2006.01)
*G06Q 50/02* (2012.01)
(Continued)

(52) U.S. Cl.
CPC ....... *A01K 29/005* (2013.01); *G06Q 10/0833* (2013.01); *G06Q 50/02* (2013.01);
(Continued)

(58) Field of Classification Search
CPC .. A01K 29/005; G06Q 10/0833; G06Q 50/02; H04L 9/0637
(Continued)

(56) References Cited

U.S. PATENT DOCUMENTS 6,166,637 A * 12/2000 Cyr ...................... A01K 11/006
119/51.02
2013/0018761 A1 * 1/2013 Kwak ................ G06Q 30/0201
705/26.61
(Continued)

FOREIGN PATENT DOCUMENTS

GB 2553262 A * 3/2018 ............... A01K 7/00
GB 2553262 A 3/2018
(Continued)

OTHER PUBLICATIONS

International Search Report and Written Opinion, PCT/US2019/030970, dated Jul. 26, 2019.

*Primary Examiner* — Omar Casillashernandez
(74) *Attorney, Agent, or Firm* — Jackson Walker LLP

(57) ABSTRACT

Food supply may be tracked, authenticated, and evaluated by a variety of systems, processes, and techniques. In certain implementations, computer systems at various animal producers in the food supply chain (e.g., ranch and feedlot) may record and generate data regarding an animal (e.g., breed, age, location, hydration regimen, health history, etc.) and report this to a server system, which may process the data in an authenticated manner. Entities further down the chain (e.g., retailers) may access the server system to retrieve information about meat products and use this in sales efforts. Consumers may also retrieve information about meat products so that they may make informed buying decisions. Additionally, feedback may be provided to animal producers regarding the meat, which may encourage them to continue producing quality animals. Data may also be monetized, and a portion reinvested back to the food producer to assist in labor costs associated with system compliance.

19 Claims, 9 Drawing Sheets

(51) Int. Cl.
*H04L 9/06* (2006.01)
*G06Q 10/08* (2012.01)

(52) U.S. Cl.
CPC ....... *H04L 9/0637* (2013.01); *G06Q 2220/00* (2013.01); *H04L 2209/38* (2013.01)

(58) Field of Classification Search
USPC .............................................. 340/573, 573.3
See application file for complete search history.

(56) References Cited

U.S. PATENT DOCUMENTS

| | | | | |
|---|---|---|---|---|
| 2014/0074742 | A1* | 3/2014 | Pratt | A01K 29/00 |
| | | | | 705/333 |
| 2016/0063188 | A1* | 3/2016 | Thornberry | H04L 63/08 |
| | | | | 705/3 |
| 2017/0202185 | A1* | 7/2017 | Trumbull | G16H 40/67 |
| 2018/0114168 | A1* | 4/2018 | Ryan | G06Q 10/06315 |

FOREIGN PATENT DOCUMENTS

| | | | |
|---|---|---|---|
| KR | 10-0817387 | * | 3/2008 |
| KR | 100817387 | | 3/2008 |

\* cited by examiner

FOOD SUPPLY TRACKING, AUTHENTICATION, AND FEEDBACK SYSTEM

RELATED APPLICATIONS

This application claims priority to U.S. Patent Application No. 62/666,985, entitled "Food Supply Tracking, Verification, and Feedback System" and filed May 4, 2018. This prior application is incorporated by reference in its entirety.

TECHNICAL FIELD

This invention relates in general to management of animals and, more particularly, to comprehensive systems and methods for tracking, verifying, and providing feedback regarding animals in the food supply chain.

BACKGROUND

Feeding facilities (e.g., feedlots or feed yards) are critical to the world's food supply. But managing them efficiently presents many challenges. For example, upon arrival at a typical cattle feedlot, each member of the herd will make at least one trip through a chute, where handlers often can afford to spend only about 45 seconds processing each animal. Initial processing typically involves some variation of each of the following: (1) standard treatment such as spraying, deworming, and antibiotics; (2) when feasible, some level of assessment and any special treatment that may be indicated based on the assessment; and (3) identification by attaching either an RFID ear tag, a numbered or bar-coded ear tag, or some other form of individual animal identification. Other processing activities can include vaccination, castration, horn-tipping, weighing, etc., all of which can help in managing the herd. Naturally, with whatever processing takes place, records also need to be created, updated, and transferred for each cow (e.g., calf, heifer, steer, bull, etc.) being processed.

Challenges arise from the need for speed versus trying to determine what particular type of treatment is needed for each individual cow, which can be quite difficult. When a feedlot omits a critical treatment, it can quickly lose a large part of the herd.

In the United States' cattle industry, annual mortality of cattle due to disease is estimated to be in the hundreds of millions of dollars. A reliable method of determining the health of a cow or the presence of disease is by assessing the body temperature of the animal. In the case of infections, environmental factors, or toxins, a cow's temperature will elevate. These elevations are diagnostic to veterinarians in the diagnosis of disease and disease conditions in cattle. In the day-to-day production of cattle, the evaluation of the presence of increased body temperature or fever is underutilized due to time constraints and the need to physically restrain the animal. This underutilization of temperature evaluation delays the diagnosis of disease and therefore increases the ineffective uses of medications and loss of animals.

So, rather than attempt to predict which cows need treatments and which do not, the feedlot industry is constantly facing temptations to mass treat all animals entering a feedlot as a precaution. But mass antibiotic treatment of an entire herd of potentially at risk cattle is not only expensive, it presents a litany of concerns for beef quality and microbial mutation. Regulatory agencies (e.g., FDA or USDA, under Presidential Executive Order 13676) recognize the pending microbial resistance public health crisis (as outlined by WHO and other world agencies) and therefore strongly discourage overuse of antibiotics in order to minimize the risk of microbial mutation, practically outlawing Gentamicin Sulphate and blended cocktail treatments for use in bovine applications. In addition, consumers show a strong demand for beef, as well as other livestock, that is free from additives and antibiotics, and was raised in a more environmentally friendly way. Thus, there has long been a huge need to improve herd processing through more accurate assessments and more intelligent treatments.

Other herd management practices have been advancing more systematically than livestock assessment techniques, particularly in the area of livestock tagging. Tags applied to each cow are used to identify the particular cow and are typically applied in the ear where they can be readily seen and tracked. Radio Frequency Identification ("RFID") technology is now being utilized to a greater extent in the agricultural industry. Also, more and more historical data is being required by regulatory agencies before a cow, as well as other livestock, can be slaughtered or packed.

At least three companies have attempted to help ranchers manage cattle based on temperature, but their attempts have been less than ideal. Tekvet [website: tekvet.com], Fever Tags LLC [website: fevertags.com], and Quantum Ag Products have launched systems of mobile temperature monitors (e.g., a surface-based thermistor mounted in the calves' ears and a temperature sensor in the calves' ear, respectively), which link to a base station.

Other efforts have been directed at using the core (i.e., internal) temperature, or more precisely the temperature of the blood as it flows in or near the pulmonary artery near the heart, to determine health. Unfortunately, core temperature has been difficult to measure accurately without invasive placement in the sensitive interior of the body. Bella AG has an invasive sensor, Bolus, but it has proved difficult to scan.

SUMMARY

The food supply chain may be managed by a variety of systems, processes, and techniques. In particular implementations, the items in the food supply chain (e.g., animals and meat) may be tracked, verified, and reviewed.

In certain implementations, computer systems at various points in the food supply chain (e.g., ranch, farm, feedlot, and packer) may record and generate data regarding an animal (e.g., breed, age, geographic origin, feed regimen, hydration regimen, inoculation history, movement history, health history, etc.) and report this to a server system, which may be a dedicated server at a particular location or be cloud based (e.g., on Microsoft Azure). The server system may process the data so that it may be later authenticated (e.g., via blockchain). Entities further down the food supply chain (e.g., distributors and retailers) may access the server system to retrieve information about meat products and use this in marketing and sales efforts. Consumers may also retrieve information about meat products so that they may make an informed decision regarding buying meats. Additionally, feedback may be provided to animal producers (e.g., ranches, farms, and feedlots) regarding the meat, which may encourage them to continue producing high quality animals.

Various systems, processes, and techniques described herein may have one or more features. For example, being able to track animals provides the ability to identify animals with health conditions (e.g., sick) in an automated and individualized manner. This reduces the amount of visual inspections that have to be performed on the animals and increases accuracy of identification. Moreover, it allows animals that are sick to be treated properly and removed from those that are not sick in order to prevent the spread of the sickness, and it allows an informed decision regarding those that are healthy enough to continue without inoculation. This results in early intervention for animals that actually need antibiotics or other treatments and also informed management of the overall livestock based on objective, newly developed standards and reduced inoculations. This should provide higher quality animals, lower death loss, increased livestock operation profitability, and potential cost savings, as well as reduce the environmental footprint of large livestock operations (e.g., feedlots). Furthermore, it should result in high quality meat for consumers. Data may also be monetized, and a portion reinvested back to the rancher, farmer, feedlot, or packer to assist in labor costs associated with system compliance.

A related feature includes allowing feedlots to avoid over-treating a herd and focusing instead on pinpointing animal health. For example, providing treated water to well livestock may also improve overall general health benefits.

Still other implementations relate to products made by the described processes as well as apparatus, systems, and techniques for performing all or part of such processes. Since there are many alternative variations, modifications and substitutions within the scope of the invention, one of ordinary skill in the art should consider the protected scope of the invention from a review of the claims appended hereto as considered in the context of the prior art and the various descriptions of this application.

Many other features will be evident from the remainder of this application in light of a more exhaustive understanding of the numerous difficulties and challenges faced by the prior art, which in turn will be evident to those skilled in the art.

BRIEF DESCRIPTION OF THE DRAWINGS

For a more complete understanding of the present invention and its implementations, and the features thereof, reference is now made to the following descriptions taken in conjunction with the accompanying drawings, in which.

Like reference numerals are used for similar elements of various embodiments.

DETAILED DESCRIPTION

Food supply may be managed by a variety of systems, processes, and techniques in an effort to improve its quality and provide a verified food supply chain. While the inventive concepts are much more basic than any particular implementation, one skilled in the art can gather a partial appreciation for some of the possible benefits of the broader concepts and possible interplay between various elements of the concepts in the course of considering example implementations, some of which are described in detail below.

Figure 1:
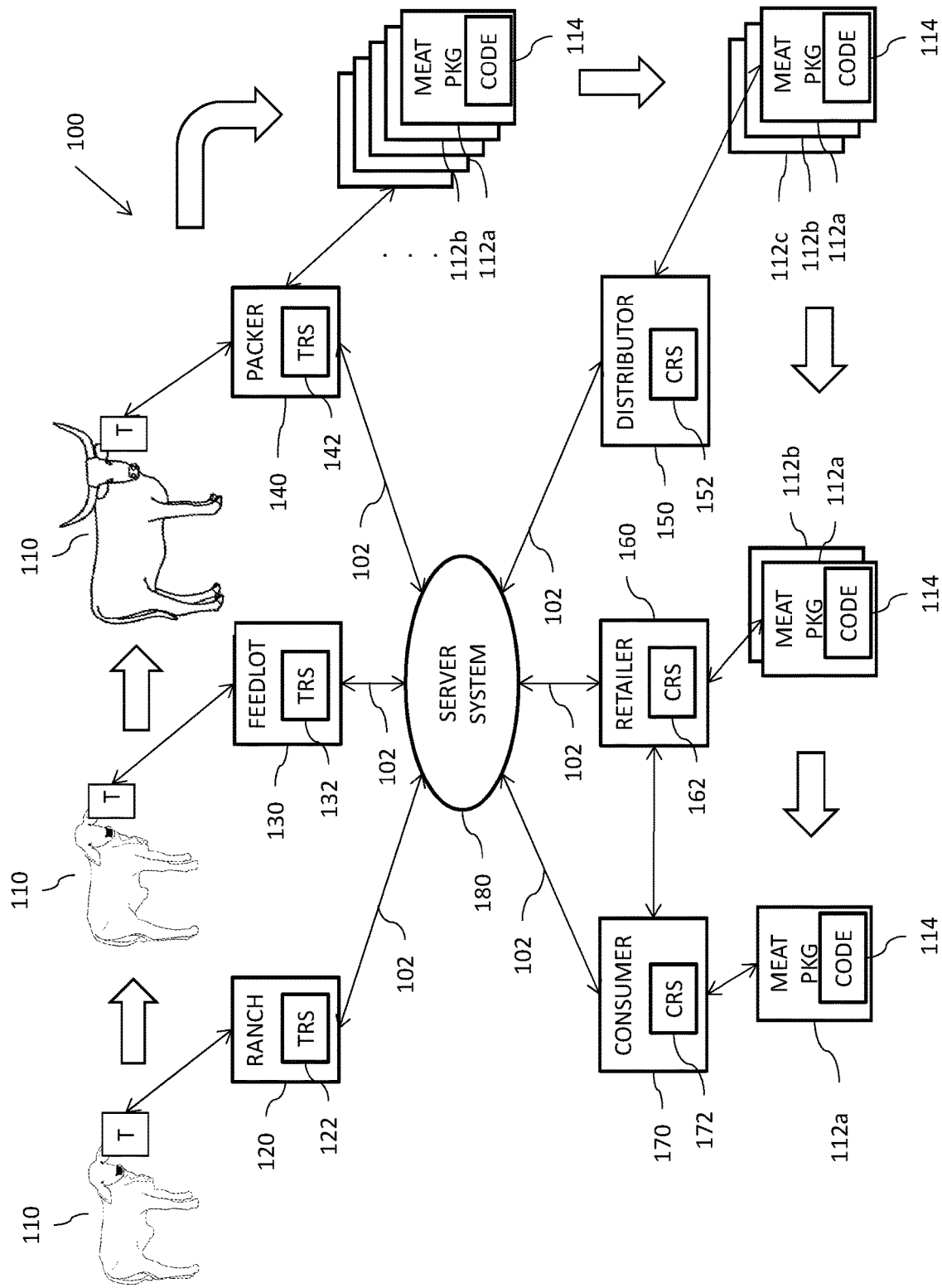
FIG. 1 is block diagram illustrating selected components of an example food supply tracking, verification, and feedback system.

FIG. 1 illustrates selected components of an example food supply tracking, verification, and feedback system 100. Among other things, system 100 includes an animal 110 that is tracked throughout the food supply chain. As illustrated, animal 110 is a bovine, but it may be other types of appropriate livestock (e.g., sheep, goat, pig, chicken, turkey, etc.). The data regarding animal 110 may begin when the animal is quite young (e.g., a few weeks old) and continue to be gathered throughout the animal's life, processing, and distribution to the ultimate consumer. The time from the animal's introduction into the system, its raising, its processing into meat, and the delivery of the meat to the consumer is referred to herein as the animal's lifecycle.

A typical first data gathering operation begins at a ranch 120 (or farm) where the animal is raised—for example, when animal 110 is a baby (e.g., a calf). Animal 110 may be identified by age, breed, sex, markings, etc. Moreover, data may be gathered regarding the animal's feeding regimen and vaccinations.

As illustrated, animal 110 may be tagged with an tag T. In the illustrated implementations, tag T is an ear tag, but it may be another type of tag in other implementations (e.g., an RFID chip, a collar tag, or an ankle tag).

Tag T will have a unique identifier (e.g., an alphanumeric code) that may also be used to identify animal 110. Among other things, tag T may facilitate tracking the animal's movement, body functions (e.g., temperature), and/or behavior to determine whether the animal is healthy. Tag T may communicate wirelessly with a tag reader system 122 at ranch 120 regarding the collected data. This data, along with the animal identifying data, may be sent to a server system 180 that collects data over the lifecycle of animal 110. Server system 180 may be a single server or a collection of servers working together (e.g., at a server farm or in a distributed manner). In particular implementations, server system 180 may include one or more cloud-based servers.

Tag T may allow the location of each animal to be determined. For example, based on time of arrival of signals from the tag, the position of an animal may be determined by a tag reader system (e.g., by trilateration), or the tags themselves may determine position based on Global Positioning System (GPS) measurements by the tags. As another example, short-range tags (e.g., using radio-frequency identification (RFID)) may be monitored as the animal moves around the pen (e.g., to water and feed). UHF RFID readers, for example, may have a range from about one meter to several tens of meters. If the tag T is in range of a corresponding gateway (e.g., an RFID reader), the animal is likely approaching a location of interest (e.g., a feed or water trough).

Tag reader system 122 may be any system that can read a tag and process data regarding the tag. Tag reader system 122 may, for example, include a tag reader, whether radiofrequency-based (e.g., an RFID reader), optical-based (e.g., a barcode reader), or otherwise, and a local computer system (e.g., processor, memory, and input/output interface).

The tag may communicate with wireless transceivers in a passive or active manner. In a passive manner, the tag may be energized by signals from wireless transceivers and use this energy to transmit its identifier, along with any other information (e.g., data about the associated animal or the functioning of the tag), back to the wireless transceivers. In an active manner, the tag may generate its own power (e.g., by chemical reaction, as in a battery, for example) and transmit its information to wireless transceivers (e.g., when requested or on a schedule). Using power-assisted RFID, where the signal from the reader is used to awaken the tag but the tag responds using its own power, may help conserve power and provide a long operational life (e.g., 3-5 years). The data that is stored may be transmitted through the wireless transceiver to server system 180.

In particular implementations, tag T may use radio-frequency identification (RFID) techniques. RFID chips may store identifiers for an animal and/or information history on the animal. Suitable RFID chips are available from Allflex of Dallas, Tex. (USA) and NXP Semiconductors of Eindhoven, North Brabant (Netherlands).

The communication between tag T and wireless transceivers may be accomplished by any of a variety of wireless protocols. In particular implementations, ISO 13157 techniques may be used. In other implementations, other protocols (e.g., IEEE 802.11, IEEE 802.15, Bluetooth, etc.) may be used.

When animal 110 is old enough (e.g., about 9-15 months), it may be shipped to a feedlot 130, where it will continue to be raised. Animal 110 may be scanned as it departs ranch 120. Upon arrival at feedlot 130, animal 110 may be scanned by a tag reader system 132, and its status (e.g., location) uploaded to server system 180. Tag reader system 132 may, for example, include an RFID reader and a local computer system.

Some animals may arrive at feedlot 130 without a tag or have a non-compliant tag. If so, they may be tagged at the feedlot, and their data may be uploaded to server system 180 at that point.

Tag T or a separate tag may also be readable visually (such as a barcode or simply a number or color), as well as wirelessly to facilitate the sorting and management of the herd in the pens. In particular implementations, tag T may be color coded based on which population the animal falls into at the time. For example, the animals may be divided into: 1) an asymptomatic group (tagged as green); 2) a subclinical group (tagged as yellow); and 3) a clinical group (tagged as red). The tags could also be associated with pens. For example, a green tag could be used for a first pen, a yellow tag could be for a second pen, and a red tag could be used for a third pen. Later, when a handler or veterinarian reassesses an animal, the colored tag would be available as an accessory marker to be used on the animal where visual tracking and sorting is needed. This could also be used in selected fields by a rancher or a dairy farmer as a visual ID on the animal when utilizing the device as an everyday health tool.

At feedlot 130, animal 110 may be classified based on its health (e.g., based on temperature and/or veterinary diagnosis) and placed in an appropriate pen (e.g., healthy, potentially sick, or sick). Animals that are sick are typically given antibiotics, and this data is uploaded to server system 180. For example, cows may fall into three populations: 1) an asymptomatic group (temperature below 104 degrees F.) (e.g., low risk); 2) a subclinical group (temperature between 104-105 degrees F.) (e.g., medium risk); or 3) a clinical group (temperature above 105 degrees F.) (e.g., high risk), which typically require multiple treatment days. In some feedlots, new arrivals are placed in a quarantine pen before being placed into the main feedlot.

For example, a system could utilize a first treatment regimen for animals tagged with a green tag, a second treatment regimen for animals tagged with a yellow tag, and a third distinct regimen for animals tagged with a red tag. For instance, green-tagged cows (e.g., low risk) could generally receive no treatment or affordable/minimal treatment such as Biomycin. Yellow-tagged cows (e.g., medium risk) could receive a slightly more aggressive treatment such as Baytril, which is only indicated for bovine respiratory disease (BRD) associated with certain microbial species. Red-tagged calves (e.g., high risk) could receive even more aggressive treatment such as the combination of Draxxin together with Banamine, as well as direct oversight by a veterinarian.

In some implementations, ranch 120 and/or feedlot 130 may provide specially treated water (e.g., high pH, negative oxidation reduction potential (ORP), and/or micro-clustered) to sick and potentially sick cows in order to prevent them from needing treatment or extensive treatment. Case studies have shown that animals receiving this type of water have improved health, sometimes rapidly. Animals that are healthy may be placed in a pen and receive regular water or receive specially treated water (e.g., to prevent them from becoming sick).

In certain implementations, potable water may be processed via ionization to have a relatively low (i.e., negative) oxidation reduction potential (ORP) and a relatively high pH (i.e., above 8.5). The ORP of the water from the water treatment system may be less than −200 mV and, in particular implementations, may be less than −400 mV. A negative ORP provides a large number of negatively charged ions that provide antioxidant potential. Antioxidants work by slowing or preventing the damage caused by free radicals, which can lead to, among other things, cell dysfunction. Cows, for example, can have an overload of free radicals due to the stress of being shipped and/or being sick. The pH level of the water from the water treatment system may be above 8.0 and, in particular implementations, may be above 9.0. This may help to lower the acidity level in the cow, especially if the cow is not in homeostasis. The water may also be ionized (e.g., micro-clustered). In particular implementations, the water molecules have a hexagonal structure, which is more acceptable to plants and animals. This makes the water more bioavailable (e.g., efficient in the uptake of water to the lifeform and at carrying minerals).

In particular implementations, a water treatment unit may treat potable water by electrolysis. In electrolysis, water is run between metal plates (e.g., titanium or copper) that are being subjected to an electrical charge. Example electrolysis water treatment units are available from Enagic, Co., Ltd. of Nago (Okinawa), Japan.

In certain implementations, the water treatment unit may produce relatively high pH water and relatively low pH water. The relatively high pH water from a water treatment unit may have a pH above 8.0 and, in particular implementations, may have a pH above 9.0. In certain implementations, the water may have a pH between 8.5-9.5. The relatively low pH water from the water treatment unit may have a pH below 6.0 and, in particular implementations, may have a pH below 5.0. In certain implementations, the relatively low pH water may have a pH between 4.5-5.5. The low pH water may also be electrolyzed (e.g., have a positive charge). This low pH water may be used in animal containment areas (e.g., pens, stalls, cages, etc.) to kill bacteria and other infectious matter for cleansing the areas and treating the areas for healthier animal food production procedures. Low pH water may, for example, be especially beneficial in dairy, swine, and poultry operations. Low pH water may also be useful for watering plants.

While at ranch 120 or feedlot 130, the health of animal 110 may be monitored via tag T. For example, the tag may monitor the movements, hydration regimen (e.g., drinking frequency, drinking dwell time, and type of water consumed), and/or health indicators (e.g., temperature) of the animal and report the data to a local computer system. The data may be acted on by the operator if an animal is becoming sick (e.g., moving the animal to a quarantine area and, potentially, supplying antibiotics). The data is also uploaded to server system 180. Other data that may be uploaded includes feeding regimen and weight gain.

While at ranch 120 or feedlot 130, the local computer system may send data about an animal to server system 180. For example, the local computer system may monitor the location of the animal, and server system 180 may use this to estimate how much water the animal drank over a certain period (e.g., one day) and use this to determine whether there is a potential problem with the animal. If the number of visits and/or consumption time is out of line for the animal or the population using the water trough, server system 180 may determine that there is a potential problem with this animal. Server system 180 could then generate an alert for a user device. Representations of the animals may be displayed on the user device, using web application logic, according to their health status (e.g., green for healthy, yellow for potentially sick, and red for sick).

In some implementations, a local database may store data regarding the animal as well as the server system. Thus, both the local database and the server system may keep an event history for each tag/animal. From this data tracking, either or both of the local database or the server system may determine when an animal needs attention so that the caretaker (e.g., owner, superintendent, or veterinarian) can be alerted. The potentially sick animals may then be evaluated and placed in a hospital pen if needed. The system may also track if the animal is placed in a hospital pen.

In certain implementations, tag T may convey position data regarding the associated animals to the local computer system, which may send it to server system 180. For example, the tag may determine and store the location of the animals (e.g., by GPS measurements) and pass this to the local computer system. The local computer system or server system may, for instance, analyze the overall movement of an animal over a period of time (e.g., a day). For example, the distance that the animal traveled during the day may be analyzed. The distance could be analyzed by itself (e.g., against a threshold) to determine whether the animal is behaving abnormally or in comparison to other animals in the same pen, in some type of statistical variance (e.g., an analysis of variance analysis).

For animals that are behaving abnormally, the local computer system or the server system could analyze the location history for the animals. A variety of factors may affect the movement of cows over the course of a day (e.g., heat, cold, rain, etc.). Thus, just because an animal does not move much during a day does not mean it is ill. However, over the course of several days, this may provide a good indication. Moreover, if the animal's movement is well outside the norm relative to the rest of the herd (e.g., outside three standard deviations), an indication may be provided.

The local computer system or the server system may determine the health status for animals that are behaving abnormally. For example, if the water consumption and/or movement of the animal is below a certain threshold (e.g., an animal has consumed less than a certain amount of water and moved less than a certain distance for more than two days in a row), it indicates that the animal is potentially unhealthy. If an animal is extremely outside a threshold, it almost certainly indicates that an animal is sick, and at least potentially unhealthy. The health status of animals may be divided into a variety of classifications.

The local computer system or the server system may determine whether any animals have had a change in their health status. For example, when an animal arrives at system 100, it may be classified as healthy. However, if it is now classified as potentially sick or sick, the health status would have changed. If the health status of one or more animals has changed, an alert may be generated for those animals. The alert may, for example, be a message delivered to a user device (e.g., by e-mail) or a posting to a web-site or web application.

The server system may also monitor whether an animal has been moved to a different pen (e.g., a quarantine pen). This may validate that the feedlot is treating its animals appropriately and/or indicate to the server system that an animal is sick.

In certain implementations, the local computer system or the server system may designate certain animals or groups of animals for receiving treated water. For example, potentially unhealthy or sick animals may be designated. As another example, female cows that have recently been bred may be provided with treated water (e.g., negative ORP and/or high pH). This may have the effect of increasing the immune system. The water may be provided to an animal individually or to the animal as part of a larger group.

A tag reader system may also determine the health status of the animal before determining whether to inject additional treated water. In particular implementations, the local computer system may receive data (e.g., from server system 180) regarding which animals are potentially unhealthy or make this determination itself. This data may, for example, be stored in a table in a database and indexed by animal identifier. When an animal is detected by a proximity sensor (e.g., a patch antenna), the proximity sensor may read an identifier for the animal (e.g., from a code in an RFID chip or an optical code on a tag) and convey this to the local computer system. The local computer system may then check the identifier against the data and determine whether the animal is potentially unhealthy. If there is no indication that the animal may be unhealthy, the local computer system may take no action regarding the water in the trough. If the animal is potentially unhealthy, however, the local computer system may command that treated water be injected into the trough. This should rapidly adjust the properties of the water to even more beneficial levels (e.g., from −200 mV to −400 mV). In particular implementations, the ORP of the water may go as low as −900 mV, or even −1,100 mV, especially when the treated water is first injected, although it typically does not stay at that level for long periods.

Over time, the animal will grow at the feed lot and, eventually (e.g., after about six to nine months), be sent to a packer 140. Animal 110 may be scanned as it departs feedlot 130. Upon arrival at packer 140, animal 110 will be scanned in via its tag T by a tag reader system 142. Tag reader system 142 may, for example, include an RFID reader and a local computer system. Animal 110 will then be processed into meat, which is apportioned into packages 112. A package 112 may, for example, be an individually wrapped piece of meat or a box of meat.

Each package 112 will be provided with a code 114 (e.g., a barcode, whether linear, matrix, or otherwise) that will link the identity of the meat in the package back to animal 110 (e.g., using graph transversal). Thus, the life history, or at least a part thereof, of the meat in a package 112 may be readily acquired.

In certain implementations, each package 112 may contain a unique code 114. One or more components of system 100 (e.g., server system 180) may map the code 114 on a package 112 back to the originating animal. In some implementations, a package may contain meat from multiple animals 110. As long as the animals were raised similarly (e.g., approximately the same age and on the same ranch) and contain similar health profiles (e.g., always healthy), grouping meat from different animals in a package 112 should not present a problem. The code 114 may be mapped back to each animal in the package or to a batch of animals (e.g., from a ranch 120). In certain implementations, the identifiers of the animals in a batch can be mapped to the identifiers that the processor has (e.g., batch and lot codes).

Computer systems at packer 140 may generate the codes 114 in conjunction with the rest of system 100. For example, using system integration, code generation software may be used at packer to generate codes that are specific to their operations.

Packer 140 may provide various data regarding an animal. For example, the packer may indicate when the animal arrived, when it was slaughtered, what USDA lot code was in effect that day, what the internal packer meat batch is for that animal, what table the animal was cut on, the incoming animal weight, and/or the carcass weight. They may also input the USDA program that the animal is affected by (e.g., Kosher, Certified Angus, etc.).

From packer 140, meat packages 112 may be sent to a distributor 150. Meat packages 112 may be scanned as they depart packer 140. At distributor 150, meat packages 112 may be scanned in by a code reader system 152 and reported to server system 180. Code reader system 152 may include any system for reading a code from a meat package 112 and processing the data therefrom. Code reader system 152 may, for example, include a code reader (e.g., a barcode scanner or an RFID reader) and a local computer system (e.g., processor, memory, and input/output interface). Server system 180 may then inform distributor 150 what type of animal was used to produce the meat in the packages 112. Distributor 150 may use this information in marketing and distributing meat packages 112.

From distributor 150, meat packages 112 may be sent to a retailer 160 (e.g., a grocery store, a meat market, or a restaurant). Meat packages 112 may be scanned as they depart distributor 150. At retailer 160, meat packages 112 may be scanned in and reported to server system 180 by a code reader system 162. Code reader system 162 may, for example, include a code reader (e.g., a bar code scanner) and a local computer system. Server system 180 may then inform retailer 160 what type of animal was used to produce the meat in the packages 112 (e.g., breed, age, inoculation history, breeding history, health history). Retailer 160 may use this information in marketing and selling meat packages 112.

At retailer 160, a consumer 170 may acquire data regarding the meat in one of packages 112 by scanning the package with a retailer-provided code reader system or a consumer-provided code reader system 172. Code reader system 172 may, for example, be a hand-held system (e.g., a smart phone). The data may be retrieved from the computer system of the retailer 160 or directly from server system 180 (e.g., over a WiFi or cellular link). Using this data, the consumer may confirm the representations made about the meat (e.g., no antibiotics or artificial growth hormones administered, antioxidant water consumption, and packaging date) as well as acquire additional information about the animal from which the meat was produced (e.g., breed, geographic location, age, farmer or rancher, operation type, etc.). Using this data, the consumer may decide whether to purchase the meat or not. The consumer may also acquire this data directly from server system 180 when outside the retailer (e.g., at their residence).

If the consumer chooses to buy a meat package 112, the meat package is typically scanned as it leaves retailer 160 (e.g., at a checkout counter). After leaving the retailer, consumer 170 may provide feedback regarding a meat package 112 using code 114. For example, a consumer may provide feedback regarding the freshness, quality, taste, and cut of the meat in a package 112. This information may be sent to server system 180 for association with the particular animal, ranch, feedlot, packer, distributor, and/or retailer. Using this information, analysis may be made of which of these entities are producing the appropriate quality of meat for consumers in the appropriate manner, which reinforces the customer's purchasing decision. Moreover, using machine learning, appropriate factors for producing different types of meat may be determine and applied to future animals. Additionally, this feedback may be used to reinforce the importance of maintaining high standards by all of these entities. For example, feedback from consumers may be provided to the rancher with positive reports on how people are receiving their meat, to restaurants with more objective feedback on the quality of the experience at the restaurant, and to grocery stores with information on what they should keep in stock based on predicted demand (e.g., shares, posts on social media, quality of the feedback).

In some implementations, when a consumer purchases a meat package 112, retailer 160 may provide a monetary payment back to ranch 120. For example, a portion of the revenue on an ad click could be sent to back to ranchers who chose to share a portion of the data from their animals. The payment could be linked to the tier of data that a rancher chose to share. Thus, data may be monetized, and a portion reinvested back to the rancher, farmer, feedlot, and/or packer to assist in labor costs associated with system compliance.

The reader systems of ranch 120, feedlot 130, packer 140, distributor 150, retailer 160, and consumer 170 are coupled to server system 180 through communication links 102. Each communication link 102 may include one or more wireline (e.g., LAN and WAN) and/or wireless (e.g., WiFi and cellular) links. In particular implementations, one or more of links 102 may include the Internet.

System 100 has a variety of features. For example, a detailed history of an animal may be acquired through its raising, processing, distribution, and retailing (i.e., its lifecycle). Thus, retailers and/or consumers may make informed decisions regarding which types of meat to buy and sell. A complementary benefit is that the system can encourage ranches, feedlots, and packers to produce high quality animals (e.g., without growth hormones or excessive antibiotics). As retailers and consumers will be able to readily verify the origin, raising, and treatment of animals, ranches, feedlots, and packers will have more incentives to treat animals in line with consumer expectations.

As part of treating animals in line with consumer expectations, feedlots, and to a certain extent ranches and farms, will be encouraged to use treated water that raises the pH balance of the animals and improves their antioxidant capability, helping them to fight off disease. This may result in decreased need for costly antibiotics and other pharmakinetics used in animal production and management, which will also reduce the toxic runoff (e.g., through urine) of animal byproducts by reducing drug use and overload and reduce the environmental impact of animal operations.

Moreover, by being able to control the water for animals, treated water may be provided to one or more animals in an efficient manner. The beneficial properties of treated water subside after sitting for a period of time (e.g., 1-6 days). Thus, the water in a water trough must be rejuvenated from time to time with newly treated water. And although only a fraction of the total water amount must be injected to achieve beneficial results (e.g., 5-10%), the treated water is considerably more expensive than just standard potable water. Thus, being able to inject the treated water in an intelligent manner provides appropriate water in a cost effective manner. This should provide higher quality animals, fewer herd losses, increased feedlot profitability, and potential cost savings, as well as reduce the environmental footprint of large feedlot operations.

Additionally, being able to detect the presence of animals allows the treated water to be provided when it is needed. For example, if no animal approaches the water trough for an extended period of time, the water properties do not have to be maintained at their highest levels. But when an animal approaches, the water may be quickly rejuvenated. Additionally, being able to detect the presence of animals also allows potentially unhealthy animals to receive highly preferred water (e.g., −800 mV).

System 100 also provides insight into the behavior of animals, especially those that are potentially unhealthy. By detecting the presence of animals and determining their identity, system 100 provides data on how often animals are consuming water and, in certain implementations, how much they are consuming. This may provide insight into the overall health of an animal. Moreover, it may provide early intervention for animals that actually need antibiotics or other treatments and also informed management of the overall herd based on objective standards and reduced inoculations.

System 100 also provides some levels of authentication regarding animal health. For example, system 100 may provide an indication if an animal has been sick, and therefore probably received antibiotics, even if this is not reported to the system. For example, the system may monitor animal temperature (e.g., elevated temperature relative to herd), movements (e.g., animal is not moving often enough and/or animal is not coming to water often enough), behavior (e.g., animal is lying down excessively), and/or location (e.g., animal has been placed in hospital pen) in an effort to authenticate the reported treatment history of the animal.

System 100 also provides some levels of authentication regarding meat quality (e.g., another part of the animal's lifecycle). For example, system 100 may provide data regarding when an animal was processed into meat and by what entity. As another example, system 100 may provide data regarding what distributor and/or retailer the meat was shipped too and how long it was resident there. Using this data, retailers and consumer may make judgments regarding what processors to accept meat from (e.g., those using humane and/or clean processing techniques) and the freshness of meat.

System 100 may operate without fever, additional, and/or a different arrangement of the illustrated elements. For example, a distributor and a retailer may be the same entity. In certain implementations, a packer, a distributor, and a retailer could be the same entity. As an additional example, animals may not enter the system until feedlot 130. Moreover, animals do not have to be in feedlots. For example, they could be in any type of animal maintenance or raising operation (e.g., dairies or open pasture operations).

Figure 2:
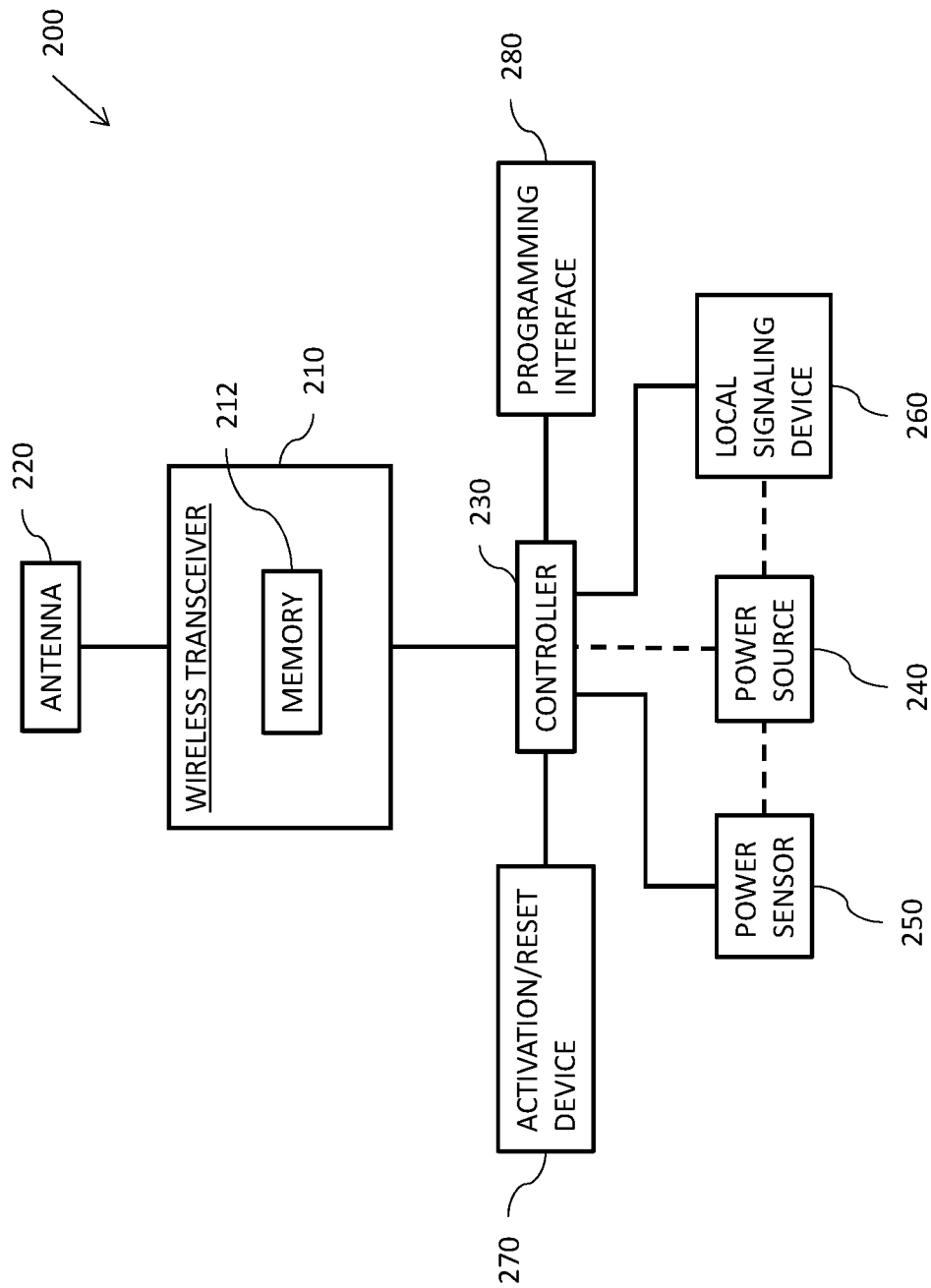
FIG. 2 is a block diagram illustrating selected components of an example animal tag for use in a food supply tracking, verification, and feedback system.

FIG. 2 illustrates selected electronic components for an example animal tag 200. Tag 200 may, for example, be worn in the ear of an animal or on an animal's collar.

In general, tags may communicate with wireless transceivers in a passive or active manner. In a passive manner, the tags may be energized by signals from wireless transceivers and use this energy to transmit their identifiers, along with any other information (e.g., data about the associated animal), back to the wireless transceivers. In an active manner, the tags may generate their own power (e.g., by chemical reaction, as by a battery, for example) and transmit their information to wireless transceivers (e.g., when requested or on a schedule). In the illustrated implementation, tag 200 uses radio-frequency identification (RFID) techniques. RFID chips may store identifiers for an animal and/or information history on the animal. The data that is stored can be transmitted through the wireless transceiver. Tags may be in place on the animals when they enter a food supply tracking, verification, and feedback system or placed on them when they enter. Suitable RFID tags are available from Allflex, and suitable RFID chips are available from NXP Semiconductors.

Among other things, tag 200 includes a wireless transceiver 210, an antenna 220, a controller 230, a power source 240. Transceiver 210 is adapted to receive and send information wirelessly using RF techniques. In particular implementations, transceiver 210 may be an RFID chip and use radio frequencies in the UHF band (e.g., around 200 MHz). Transceiver may, for example, be an SL3S4021 from NXP Semiconductors.

Wireless transceiver 210 includes memory 212 therein. The memory may, for example, be non-volatile memory (e.g., EEPROM). Memory 212 may store the identifier for the tag as well as data from controller 230 (e.g., power level, timers, tag temperature, local alert status, etc.) and from the local computer system (e.g., media record). This data may be sent by wireless transceiver 210 when the tag is within transmitting range of a tag reader.

Antenna 220 operates with transceiver 210 and is adapted to radiate and absorb RF transmissions at a certain frequency. The antenna may, for example, be embedded in a printed circuit board (PCB). Particular implementations may use two antennas.

Controller 230 is adapted to analyze RF transmissions and determine whether and how to respond. In certain modes of operation, controller 230 may respond with data stored on the tag. This data may, for example, include health and treatment data regarding the associated animal and/or data regarding the tag (e.g., power level). Controller 230 is generally a logic driven device and may, for example, be a microprocessor or a microcontroller. In particular implementations, controller 230 is an STM32L011F4U6 from STMicroelectronis of Geneva, CH (Switzerland).

Controller 230 may receive power from power source 240. Power source 240 may, for example, be a battery (e.g., a Lithium Thionyl Chloride cell).

Tag 200 also includes a power sensor 250, a local signaling device 260, an activation/reset device 270, and a programming interface 280. Power sensor 250 is adapted to sense the voltage level of power source 240 and provide a digital value to controller 230. Local signaling device 260 is adapted to be activated by controller 230. Local signaling device 260 may provide audible and/or visual alert. In particular implementations, local signaling device 260 includes a light emitting diode (LED) (e.g., an LJ CKBP-JZKZ-25-1 from Osram Opto Semiconductors of Regensburg, Bavaria (Germany)).

Activation/reset device 270 is adapted to alert controller 230 to begin and/or reset operations. Activation/reset device 270 may, for example, be a switch (e.g., magnetic or manual). In particular implementations, activation/reset device 270 may be a Reed switch. Passing a magnet over the Reed switch will cause it to close, generating a magnetic pulse to controller 230 and waking it.

Programming interface 280 allows controller 230 to be programmed. Programming interface 230 may, for example, be a serial wire debug interface.

In certain modes of operation, controller 230 may monitor how long it has been since the animal approached water. For example, the controller may use sensing of the tag by an RF sensor as a proxy for when an animal is approaching water. The controller may store when was the last time that the animal approached water in memory. Periodically, the controller may determine how much time has elapsed since the last time that the animal approached a water trough. If the period of time is too long (e.g., more than 8 hours), the controller may activate local signaling device 260.

In certain implementations, tag 200 may convey position data regarding the associated animal to a remote computer system (e.g., tag reader system 122 or server system 180). For example, the tag may determine and store the location of the animals (e.g., by GPS measurements) and pass this to the remote computer system. The remote computer system may, for instance, analyze the overall movement of a cow over a period of time (e.g., a day). For example, the distance that the cow traveled during the day may be analyzed. The distance could be analyzed by itself (e.g., against a threshold for the animal) to determine whether the cow is behaving abnormally or relative to the rest of the herd (e.g., in comparison to other cows in the same pen), in some type of statistical variance (e.g., an analysis of variance analysis).

Tag 200 may also include a movement sensor. The movement sensor may detect movements/non-movements of the animal (e.g., lying down, hanging head low, rumination), and controller 230 may store them for reporting to a remote computer system when in range of a wireless reader.

Although FIG. 2 illustrates an example tag for livestock management, other implementations may include fewer, additional, and/or a different arrangement or components. For example, a tag may include a movement sensor system, a temperature sensor, a Global Positioning System (GPS) receiver, a GPS antenna, and a long-range communication system.

A movement sensor system may be adapted to detect the movements of an animal (e.g., lying down, hanging head low, ruminating, etc.) and store them for reporting to a remote computer system when in range. A movement sensor system may, for example, include one or more accelerometers. Based on the detected movements, the controller may determine whether the animal is potentially unhealthy. For example, healthy animals typically have various movements and movement distances associated with them throughout the day. However, sick animals tend to be lethargic. Thus, by sensing an animal's movements and analyzing them (e.g., compared to previous movements of the animal or relative to movements of other animals in an area), a determination may be made as to whether an animal is potentially unhealthy.

A movement sensor system may, for example, include an accelerometer that can detect animal movements. The accelerometer may, for example, be a three-axis accelerometer, but in some implementations, a two-axis accelerometer may be used. Typically, if an animal, especially a grazing animal, is stationary too long, it is sick. For example, for cows, if they lie down less than two hours consecutively, they are typically healthy. However, if they lie down two to four hours they may be sick, and if they lie down more than four consecutive hours, they probably are sick. An accelerometer would typically register little to no acceleration, especially lateral acceleration, while the cow is lying down.

In certain implementations, patterns of movement (e.g., dropping front and then rear) may be stored and looked for to determine when an animal is lying down. Additionally, taking readings while a cow is lying downs (e.g., at night) may provide insight into when a cow is lying down in the future.

A temperature sensor may be adapted to detect the temperature of the animal. The temperature sensor may, for example, be mounted to the back side of the tag's housing so that is next to the animal's ear. Based on the detected animal temperature, the controller may determine whether the animal is potentially unhealthy. For example, healthy cow temperatures are typically between 101 and 102 degrees F. An elevated temperature (e.g., greater than 104 degrees F.) may mean that the animal is in distress. As temperature sensors are somewhat unreliable, in certain implementations, the measured temperature may be compared to previous temperatures of the animal or temperatures of other animals in an area. Comparing relative temperatures will allow accounting for temperature fluctuations that occur on hot or cold days. Moreover, comparing relative temperature for animals in close proximity may help account for local variances in groups of animals (e.g., those under a shade tree). In particular implementations, the temperature may be analyzed in combination with the animal's movements to assess whether the animal is potentially unhealthy.

A temperature sensor may, for example, be a thermistor, an analog temperature sensor, or a digital temperature sensor. For increased accuracy, these may be placed so that the temperature is measured as close to the ear attach point as possible (near the dart receptacle). A thermistor is a small 2-terminal device, so 2-wires or a small, custom, flex circuit will allow it to be positioned away from the main board to a remote location. The controller will periodically measure the thermistor and apply a non-linear correction to estimate temperature. Digital temperature sensors have the advantage of being a calibrated device with programmable threshold/wake features that would allow the main board to be alerted automatically when a threshold is exceeded.

As temperature sensors are relatively easy to implement, some implementations may use multiple such sensors (e.g., 2-3 of them) around the ear hole in case one portion of the attach tab has separated from the ear (e.g., use highest temperature reading). This could have the additional benefit of detecting loose tags, infections, etc. In particular implementations, a tag/environmental reference temperature might be useful. Thus, some implementations could include another temperature sensor on the main board (below the ear).

Measuring absolute temperature of animals using surface-mounted ear tags has proven to be difficult as the results are not consistent, and they are affected by the environment (e.g., sun, wind, rain, temperature, etc.) on external ones. Thus, internally placed tags are the most accurate, but they are difficult to implement without an invasive procedure. Surface-mounted temperature sensors, however, may provide an indication of health if they are used to provide relative temperature between animals.

For example, assume the standard healthy temperature for an animal is 100 degrees F., and it is unhealthy if it has a temperature of 104 degrees F. However, on a warm, sunny day, the temperature of an externally mounted sensor may register slightly higher (e.g., 102 degrees F.) due to the radiation from the sun and/or increased air temperature. But if all the temperature sensors suffer a similar effect then as long as an animal's temperature does not deviate greatly from the average of the group (e.g., 4 degrees F.), it is probably healthy. Thus, if on the warm, sunny day, the group average is 102 degrees F., an animal registering 105 degrees F. may be considered healthy due to a small deviation from the increased temperature of the group. This may not be its absolute temperature, but it is enough of an indication of its temperature to classify its health.

In certain implementations, a GPS receiver may be responsible for determining the geographic position of the animal. The GPS receiver may receive signals from multiple (e.g., four) satellites through antenna 850 and determines the position through trilateration and/or differential GPS.

In some implementations, a long-range communication system may send and receive data over large distances (e.g., greater than 100 m). In particular implementations, a long-range communication system may send data over a cellular communication system (e.g., GSM, CDMA, etc.). The data may be sent in-band or out-of-band.

In certain modes of operation, a movement sensor system may sense the movements of the animal and send signals representing the movements to the controller. Additionally, a temperature sensor may also sense the temperature of the animal and send signals representing the temperature to the controller. The controller may analyze the sensed movements and/or the temperature to determine whether the animal is healthy or potentially unhealthy. If the animal is healthy, the controller may continue receiving movement data and temperature data and determining whether the animal is healthy or unhealthy. The movement data and the temperature data may also be stored by the controller. This data may be conveyed to a remote system (e.g., server system 180) when requested via a communication system.

The behavior of a group of animals (e.g., movement, lying down, hanging head low, rumination, etc.) can be affected by a number of things. For example, weather is a major factor for outdoor animals. Rain, cold, wind, snow, and heat will have an effect on how the animals behave in general. In particular implementations therefore, group averages and deviations may be used to determine whether a cow is potentially sick. For example, if a group has a sudden change in behavior (i.e., is stationary for several consecutive hours), the health metrics may be adjusted to the group average. The sick metrics may also be adjusted to be above/below the average behavior. Deviations away from the average (e.g., 5%) may be used to infer that an animal might be sick, and large deviations away from the average (e.g., 10%) may be used to infer that an animal is sick.

For tags from which geographic positions of animals may be determined, positions of herd animals relative to each other may be used as a health classifier. For example, because cows are herd animals, they typically stay relative close to each other (e.g., within 150 m), although they can drift away for short periods of time (e.g., 0.5 hours to 1.0 hours). If a cow stays within 150 m of the herd or separates from the herd for less than 1.5 consecutive hours, they may be classified as healthy. However, if a cow separates from the herd between 150 m and 210 m or separates from the head between 1.5 hours and 2 hours, they may be classified as potentially sick, and if a cow separates from the herd more than 210 m or for more than 2 consecutive hours, they may be classified as sick.

In some implementations, the controller may receive queries (e.g., pings) and generate a response. The query may be directed specifically to the tag or to a group of tags (e.g., in a pen). The response may include the identifier for the tag. The response may also include data regarding the associated animal (e.g., location history, medical history, temperature history, movement history, etc.), which may be stored in memory.

If the controller determines that the animal might be unhealthy, the controller may activate a GPS receiver and command it to measure the animal's position (e.g., at regular intervals). The GPS receiver may measure the animal's position on a periodic basis (e.g., every hour, every ten minutes, every minute) or on event-driven basis (e.g., when the animal is moving).

The movement of an animal is helpful in understanding the condition of the animal in a given time period. The controller can process the position data to generate movement data or the position data can be sent to a remote computer system for analysis.

In some modes of operation, tag 200 may send data (e.g., tag identifier and/or status) on its own (e.g., without being queried). The tag may, for example, accomplish this based on a time or an event basis.

Figure 3:
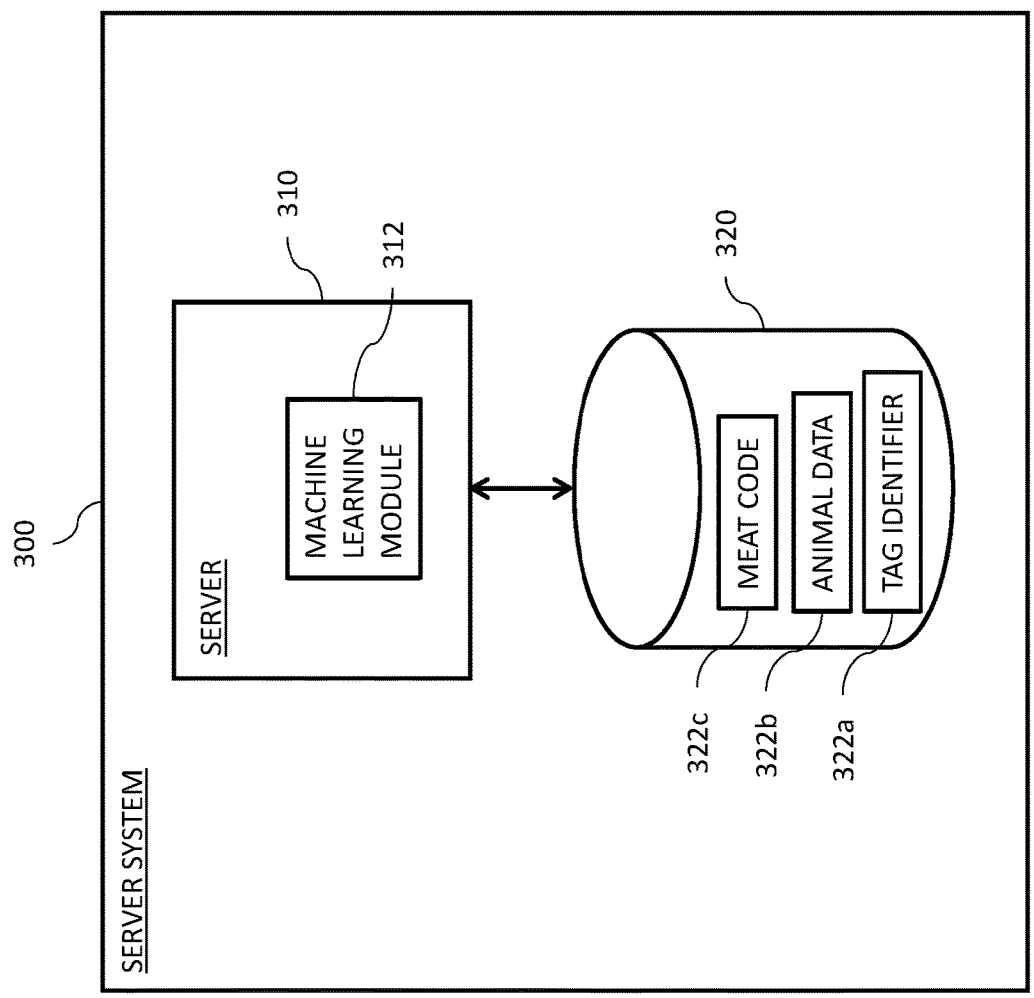
FIG. 3 is a block diagram illustrating selected components of an example server system for a food supply tracking, verification, and feedback system.

FIG. 3 is a block diagram illustrating selected components of an example server system for a food supply tracking, verification, and feedback system. Server system 300 may, for example, be a part of a system like system 100.

As illustrated, server system 300 includes a server 310 and a database 320. In particular implementations, server system 300 may include a number of servers and databases, which may be co-located or distributed. Server 310 establishes communications with various remote computer systems (e.g., at a ranch or a distributor) to receive and send data thereto (e.g., via a client-server relationship). The data received from a remote computer system is stored in database 320. Server 310 may provide the data in database 320 to a remote computer system and also analyze the data therein to generate data regarding animals (e.g., health condition) and/or operational instructions, which may also be sent to remote computer systems.

In the illustrated implementation, database 320 includes a tag identifier 322*a*, animal data 322*b*, and a meat code 322*c*, which may be stored in a flat file, a relational file, or otherwise. Tag identifier 322*a* is unique identifier for a tag (e.g., an ear tag or a collar tag) on an animal. Using tag identifier, a unique animal may be identified. The data associated with the animal (e.g., characteristics, raising location(s), health data, shipping dates, processing location, processing date, storage dates, etc.) may be stored in animal data 322*b*. Meat code 322*c* is used to identify the animal after it has been processed into meat. Meat code 322*c* also uniquely identifies the animal.

Other data that may be received by server system 300 include inoculation history, movement history, water consumption history, and feeding history. Using movement history, for example, server 310 may determine whether an animal is healthy or unhealthy, which may be timestamped.

Data at server system 300 may be analyzed by a machine learning module 312 in one or more servers to determine characteristics about an animal and/or a herd. For example, data may be analyzed (e.g., as a training dataset to a machine learning algorithm, such as AutoML from Google) to predict when an animal is well or sick. For example, animal temperatures, drinking habits, and/or movement habits may be analyzed to predict an animal's health. The resulting analytics may be stored in a matrix that may be downloaded to a tag reader system so that it can make a decision regarding animals in its locale. Additionally, the data may be analyzed to build rational for filtering unneeded random data at the tag reader system it moves up to the server system. This may improve data flow by restricting it to only what is necessary for immediate use and what is needed for future use.

In particular implementations, data may be added to server system 330 in a hashed manner (e.g., via blockchain). Thus, the existing data regarding an animal may not be changed as new data is added. A blockchain may be shared between several server system to improve its reliability.

Figure 3A:
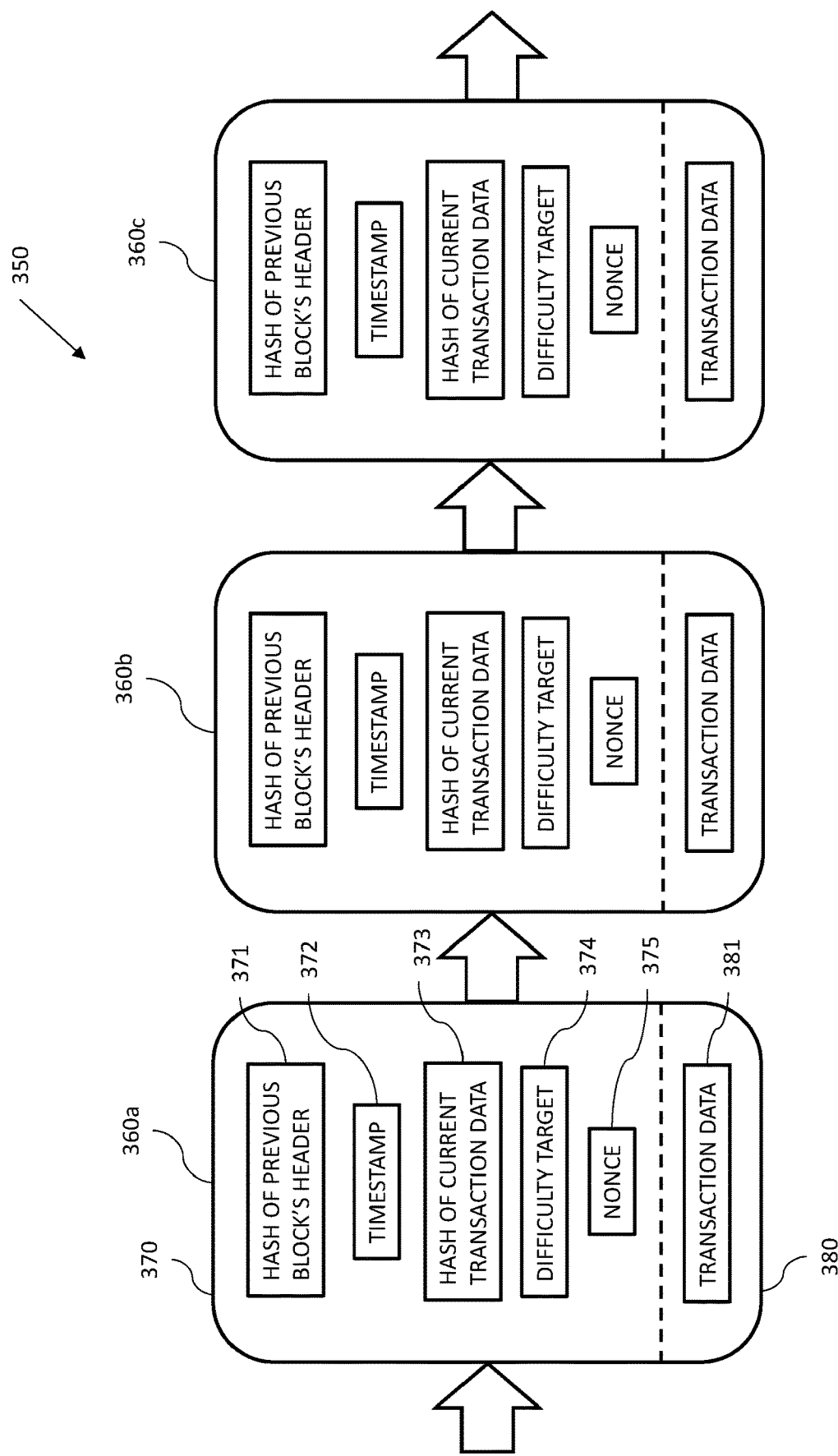
FIG. 3A is a block diagram illustrating selected components of an example blockchain.

FIG. 3A illustrates an example blockchain 350 for storing information about an animal over the course of its lifecycle. As illustrated, blockchain 350 includes a number of blocks 360 that are each validated and then linked to each other through cryptographic hashes. In general, each block 360 includes a header 370 and a body 380.

Body 380 includes the transaction data 381 that is to be immutably committed to blockchain 350. Transaction data 381 may include the data for a single transaction (e.g., animal is received at a facility or animal received a specific treatment) or for multiple transactions (e.g., multiple animals were received at a facility or multiple animals were given a specific treatment).

Header 370 includes metadata about the transaction data 381 and a cryptographic link to the previous block in blockchain 350. In particular, header 370 includes a hash 371 of the previous block's header, a timestamp 372 for when the block was created, a hash 373 of the transaction data 381 in the block, a difficulty target 374 (i.e., a target hash value for the block's header), and a nonce 375.

Including the hash 371 of the previous block's header helps to ensures that the data in the previous block becomes immutable. This is because if one wanted to change the data in the previous block, they would not only have to change the data in the previous block but also the current block since any change in data in the previous block would change the hash for that block's header, which is stored in the current block. Moreover, once a subsequent block is added onto the current block, it will not be possible to change just the data in the previous block and the current block without being detected, but it will also necessary to change the data in the subsequent block since it includes a hash of the header of the current block, which includes the hash of the previous block's header. As more blocks 360 are added to blockchain 350, it becomes harder and harder to change the data in an earlier block in the blockchain.

Hash 373 of transaction data 381, along with difficulty target 374 and nonce 375, also assists in preventing alteration of the data. Hash 373 may be a hash (e.g., MD4, MD5, SHA-1, or SHA-2) of all of the transaction data together or a hash of the hash values of all the transactions (e.g., a Merkle root).

Once the hash 373 for the transaction data is known, a hash for the header may be determined. However, the hash is typically not sufficient because difficulty target 374 sets parameters on properties the hash value of the header must have (e.g., number leading zeros). If the hash of the header does not have this value, a new hash must be determined. This is accomplished by incrementing nonce 375, which may, for example, start at zero. Each time nonce 375 is incremented (e.g., by one), the entire hash value for the header is changed. It is extremely difficult, if not impossible, to predict which nonce will produce an acceptable hash; thus, a number of iterations (e.g., millions, billions, or more) may have to be performed. Eventually, with enough iterations, a particular nonce value will produce an acceptable hash value for the header 370. Thus, changing any value in one of blocks 360, such as some of the transaction data, will require significant resources just to determine an acceptable value of the nonce to make the hash of the header acceptable. Changing some of the transaction data, for example, will cause a change in the hash 373 of the transaction data, which will then affect the hash of the block's header and almost assuredly violate the difficulty target value 374. Thus, a new nonce will have to be iteratively determined again. And, of course, this would affect the hash value of the header, which is stored in the subsequent block and also used in computing the hash value of that block's header.

Blockchain 350 provide an immutable record of actions. Since those actions are automatically gathered and input into the system, a user cannot easily fake or change them. And since the associated system may be sensing the data on the ground, it is somewhat like having a full time inspector onsite. Note that the purpose is not necessarily to show all the bad animals, but rather to allow the rancher to separate the bad ones and show off the good.

Although FIG. 3A illustrates one implementation of a blockchain 350, other implementations of a blockchain may include less or more information. For example, in other implementations, a block may include a magic number (e.g., 0xD9B4BEF9), a blocksize (e.g., in bytes), and a transaction counter. As another example, a header may include a block version number. Furthermore, an additional nonce value (e.g., extrallonce) may be stored in the transaction data (e.g., as a leaf in a Merkle tree).

Particular implementations may not use mining. Thus, the difficulty target 374 and nonce 375 may not be used.

Blockchain 350 may be stored on one or more nodes (e.g., servers) that may be localized or distributed, private or public. In a distributed environment, once a block is solved (i.e., a nonce value has been found such that a hash of its header satisfies the difficulty target), it is distributed to the rest of the computers for validation. Each node checks that the proposed block is valid, and once a consensus is reached among the nodes that a block is valid, the block is added to the blockchain, a copy of which resides at each node. Consensus on the blockchain also enforces over the entire distributed network that the events are not tampered with and are in the exact same order as they are on everyone else's computers. If one entity tries to change the ledger, and it does not match up with the rest of the ledgers, it is rejected. The blockchain may be open for all to see.

In particular implementations, the blockchain may be private (e.g., a private permissioned blockchain). The blockchain may, for instance, be on a cloud platform (e.g., Azure). For example, an instance of a Hyperledger Fabric may be installed on a private instance and 'BlockProvenance' APIs may be deployed. A private implementation may, for example, be appropriate if the stakeholders (e.g., animal distributor, animal processor, et al) have to participate in a permissioned blockchain. Each stakeholder may have an identity on the network (after authentication and authorization, for example), but not each stakeholder may have a node, which could, for example, store a ledger for the chain.

Certain data in the blockchain may be hidden from various participants. For example, if a participant (e.g., a customs official) only needs to see particular data (e.g., source and health), then only that data may be available to the participant.

The blockchain may be further protected by having the computer systems require robust types of authentication to access them. Example types of authentication include user name/password, private/public key cryptography, and JSON Web Token (JWT) and Trusted Platform Module (TPM) key generations.

A blockchain similar to blockchain 350 may be used to track an animal during its raising, its processing into meat, and the meat's delivery to a restaurant or grocer and, ultimately, the consumer. The blockchain may be updated in an automated manner. Once an animal enters a food supply tracking system similar to system 100, at a breeder or backgrounder, for example, they are tagged with a tag T, which has a unique identification and other information, such as breed, gender, and age associated therewith. When tag T is scanned (e.g., by or RFID) into the server system, this information can be committed to the blockchain, and a hash key is generated. The operation where the animal is scanned may also be recorded and stored with the animal's other information.

Within that facility, the animal may be checked into and out of different pens (e.g. early entry, residential, or quarantine), the identity of which may also be committed to the blockchain. As the animal is transferred to another facility, like a backgrounder or a feed yard, the departing animals are scanned out, and their unique codes may be associated with a batch ID, which is committed to the blockchain. At the new facility, that batch ID may be scanned in, and the unique IDs of the animals are associated with this facility via blockchain commits. There may also be a similar check in and check out procedure for the transportation of the animals, containing the driver's information instead of the operation. This transfer process may be repeated as many times as needed throughout the lifetime of the animal.

Once an animal is deemed ready for processing, it is again sent as a batch to a packer. Arriving at the packer, the individual tags T are unbatched and individually scanned for the last time as the animal is slaughtered. Animals of a specific or the same batch are processed together, to ensure that the traceability from each operation is maintained. Animals may be batched together by various criteria, including breed and location, as well as the current or historical health status of the animal. These processed batches produce several boxes of cuts per animal or animal batch, each of which is given a unique code and committed to the blockchain. Boxes containing the same cuts or containing animals from the same batch may be combined into pallets. Similar to batching cattle, the unique box codes may be associated with an overall pallet code, which is committed to the blockchain. In this manner, several pallets may also be combined into a unique truck code for their transportation, which is committed to the blockchain.

If further processing is required, the truck code is scanned at a new facility, which then associates the pallet codes, and furthermore, the individual box codes with the current facility. Similarly, the truck code may be scanned in at a warehouse, a restaurant supplier facility, or a grocer, each resulting in a new commit to the blockchain as the contents are associated with the new location. At the any given point along an animal's journey, a provenance map may be generated, which shows each of the facilities the animal has checked into throughout its lifetime. These locations are then able to generate a code that consumers may scan to show where their meat was raised. These codes may be located on menus or meat labels.

Figure 4:
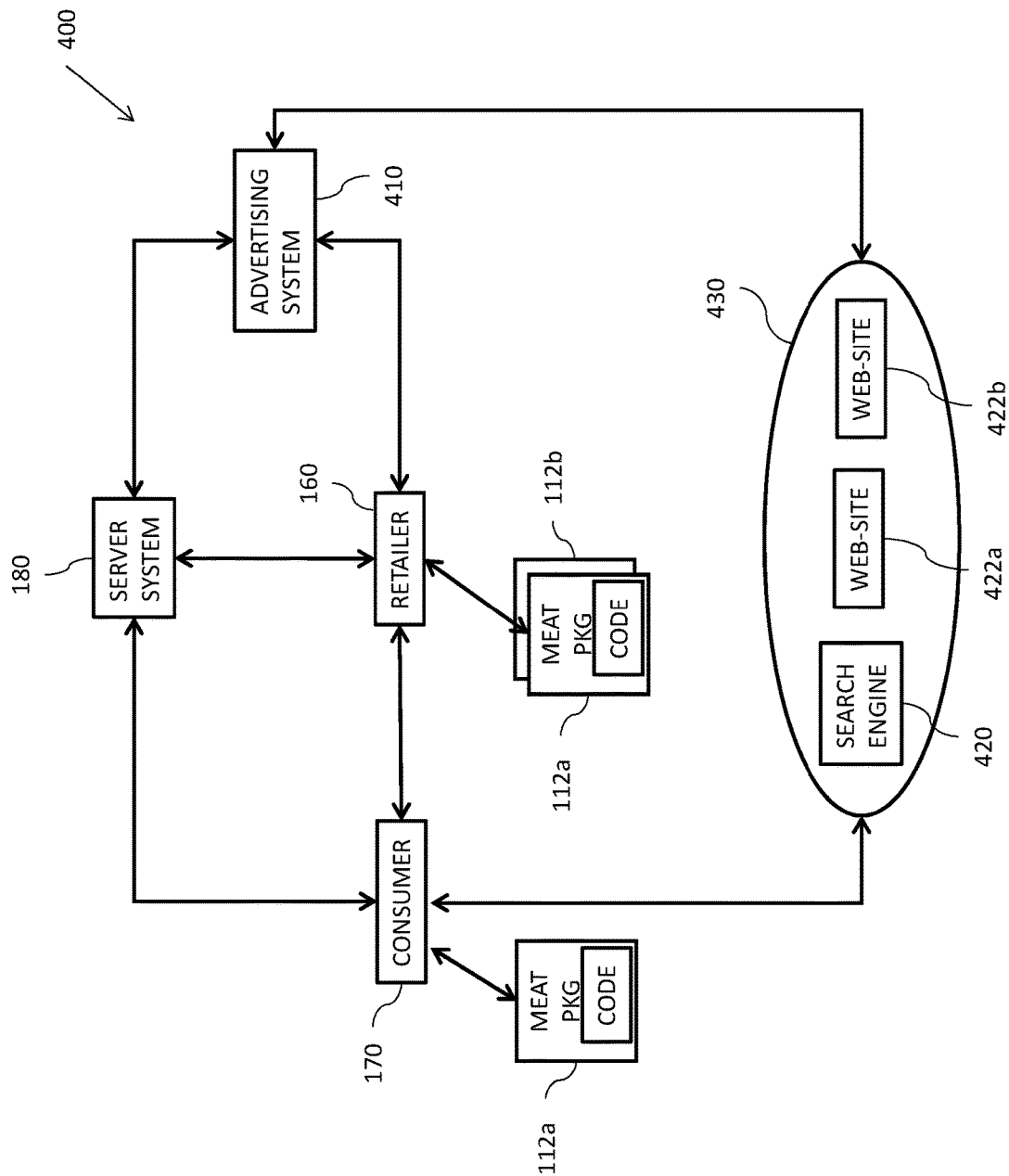
FIG. 4 is a block diagram illustrating selected components of another example food supply tracking, verification, and feedback system.

FIG. 4 is a block diagram illustrating selected components of another example food supply tracking, verification, and feedback system 400. Similar to system 100, system 400 includes retailer 160, consumer 170, and server system 180. System 400 also includes an advertising system 410 and a search engine 420 and web-sites 422 on the public Internet 430.

Advertising system 410, which may, for example, be a server system, is responsible for generating mass and targeted advertising for consumers. By accessing a computer system of retailer 160, advertising system 410 may determine what types of products retailer 160 currently has and generate advertisements (e.g., coupons) based on them. For example, if retailer 160 has a large stock of high quality, non-antibiotic meat, advertising system 410 may generate a coupon for this meat. The coupon may be presented to consumers at retailer 160 (e.g., when the meat package 112a) is scanned. Additionally, advertising system 410 may make the coupon available to search engine 420 and web-sites 422 in Internet 430.

As part of its operations in Internet 430, advertising system 410 may perform targeted advertising. Targeted advertising is a form of advertising in which online advertisers can use sophisticated methods to target the most receptive audiences with certain traits, based on the product the advertiser is promoting. These traits can be demographic, which are focused on race, economic status, sex, age, level of education, income level, and employment, or they can be psychographic focused, which are based on the consumer's values, personality, attitudes, opinions, lifestyles, and interests. They can also be behavioral variables, such as browser history, purchase history, and other recent activity. Targeted advertising is focused on certain traits, and the consumers who are likely to have a strong preference will receive the message instead of those who have no interest and whose preferences do not match a product's attribute.

One way to target ads is based on what consumers are searching for (e.g., on search engine 420). Google Adwords, for example, presents ads based on what consumers are searching for (e.g., based on word association). Another way for search engine 420 to target consumers is by remarketing. For example, Google's remarketing campaigns are a type of targeted advertising where web-sites use the IP addresses of computers that have visited their websites to remarket their ads specifically to the user who has previously been on their website as they use websites that are a part of the Google display network, or when searching for keywords related to a product or service on the Google search engine. Dynamic remarketing can improve the targeted advertising as the ads are able to include the products or services that the consumers have previously viewed on the advertiser's website within the ads. Other ways advertising campaigns are able to target the user is to use browser history and search history. For example, if the user typed in "promotional pens" in a search engine, ads for promotional pens will appear and will be targeted to the area of the user's IP address, showing the product or service in the local area or surrounding regions.

Behavioral advertising is the most common form of targeting used online. Internet cookies are sent back and forth between an Internet server and the browser, which allows a user to be identified or to track their progressions.

Cookies provide detail on what pages a consumer visits, the amount of time spent viewing each page, the links clicked on, and searches and interactions made. From this information, the cookie issuer gathers an understanding of the user's browsing tendencies and interests, generating a profile. Analyzing the profile, advertising system 410 is able to create defined audience segments based upon users with similar returned information, hence profiles. Tailored advertising is then placed in front of the consumer based upon what retailer 160 assumes are the interests of the consumer. These advertisements are formatted so as to appear on pages and in front of users to whom they would most likely appeal based on their profiles. For example, under behavioral targeting if a consumer is known to have recently visited a number of automotive shopping and comparison sites based on the data recorded by cookies stored on the user's computer, the consumer can then be served automotive related advertisements when visiting other sites 422. Thus, behavioral advertising is reliant on two forms of data, both wittingly and unwittingly, provided by consumers: 1) the delivery of advertising based on assessment of user's web movements; and 2) the examination of communication and information as it passes through the gateways of Internet service providers.

Ads may also be presented on web-sites 422 that have associated content. For example, if a web-site 422 deals with animals or meat, it may be a good target for advertising system 410 to place ads for meat packages 112. This is known as contextual advertising, in which the strategy is to place advertisements on media vehicles, such as specific web-sites or print magazines, whose themes are relevant to the promoted products. Advertisers apply this strategy in order to narrow-target their audiences. Advertisements are selected and served by advertising system 410 based on the identity of the user and the displayed content of the media.

Ads may also be presented through specific applications (e.g., on customer's smart devices). For example, ads may be presented in retailer loyalty apps (e.g., Kroger Click List and HEB Curbside Pickup). Ads may also be sent directly to customers (e.g., through e-mails).

The flowchart and block diagrams in the figures illustrate the architecture, functionality, and operation of systems, methods, and computer program products of various implementations of the disclosure. In this regard, each block in the flowchart or block diagrams may represent a module, segment, or portion of code, which can include one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or the flowchart illustration, and combination of blocks in the block diagrams and/or flowchart illustration, can be implemented by special purpose hardware-based systems the perform the specified function or acts, or combinations of special purpose hardware and computer instructions.

As will be appreciated by one skilled in the art, aspects of the present disclosure may be implemented as a system, method, or computer program product. Accordingly, aspects of the present disclosure may take the form of an entirely hardware environment, an entirely software embodiment (including firmware, resident software, micro-code, etc.), or an implementation combining software and hardware aspects that may all generally be referred to herein as a "circuit," "module," or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of a computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be a tangible medium that can contain or store a program for use by or in connection with an instruction execution system, apparatus, or device.

A computer readable signal medium may include a propagated data signal with computer readable program code embodied therein, for example in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any medium, including but not limited to wireless, wireline, optical fiber cable, RF, etc. or any suitable combination of the foregoing.

Computer program code for carrying out operations for aspects of the disclosure may be written in any combination of one or more programming languages such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the disclosure are described below with reference to flowchart illustrations and/or block diagrams of methods, apparatus (systems), and computer program products according to implementations. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other device to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions that execute on the computer or other programmable apparatus provide processes for implementing the functions/acts specified in the flowchart and/or block diagram block or blocks.

Figure 5:
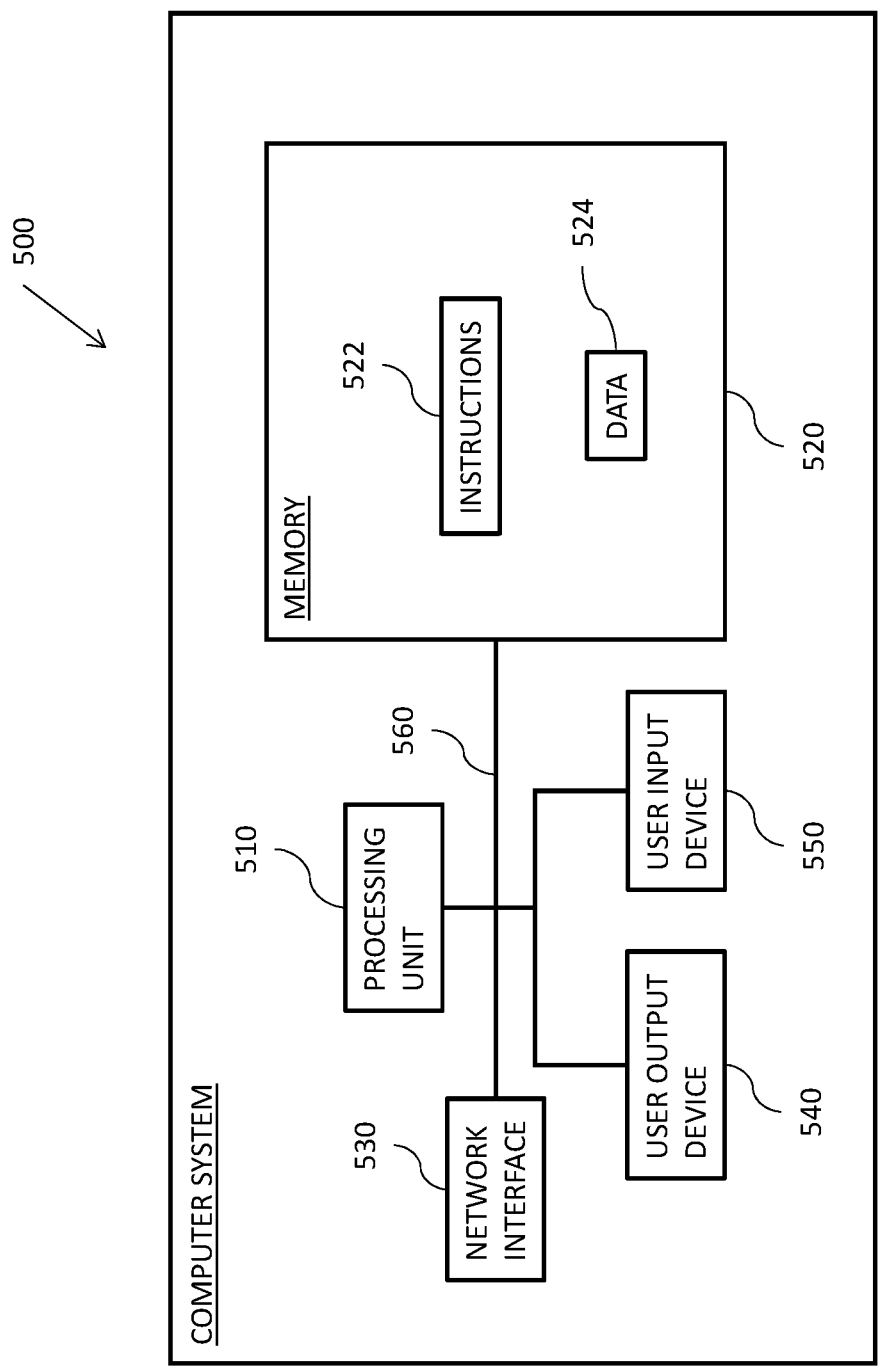
FIG. 5 is a block diagram illustrating selected components of an example computer system for food supply tracking, verification, and feedback.

FIG. 5 illustrates selected components of an example computer system 500 for performing food supply tracking, verification, and feedback. System 500 may, for example, be part of a local computer system (e.g., at a ranch or feedlot) or part of a centralized computer system (e.g., server system 180). Among other things, computer system 500 includes a processing unit 510 and memory 520, which are coupled together by a network system 560.

Processing unit 510 may, for example, include one or more processors (e.g., microprocessors, microcontrollers, field-programmable gate arrays, or application specific integrated circuits). The processors could, for instance, operate according to reduced instruction set computer (RISC) or complex instruction set computer (CISC) principles. Processing unit 510 may operate according to instructions stored in memory 520 and/or encoded on processing unit 510 itself. In general, processing unit 510 may include any number of devices that can manipulate information in a logical manner.

Memory 520 may, for example, include random access memory (RAM), read-only memory (ROM), and/or disc memory. Various items may be stored in different portions of the memory at various times. Memory 530, in general, may be any combination of devices for storing information.

Memory 520 includes instructions 522 and data 524. Instructions 522 may include an operating system (e.g., Windows, Linux, or Unix) and one or more applications. In certain implementations, applications could include a location analyzer, which may be responsible for determining locations of animals at various times and analyzing their movements, a health analyzer, which may be responsible for determining the health of animals (e.g., based on their movements), and/or a water controller, which may be responsible for controlling the generation of treated water for animals. Data 524 may include the location data and health assessments.

Network interface 530 may include one or more communication interfaces. A communication interface may, for instance, be a network interface card (whether wireline or wireless) or a modem (whether wireline or wireless). A communication interface may allow data exchange with a data network (e.g., the Internet or an Ethernet) or a phone network (e.g., a cellular network).

System 500 also includes a user output device 540 and a user input device 550. User output device 540 could, for example, be a display, a speaker, or an indicator (e.g., a light). User input device 550 could, for example, be a keyboard, a keypad, a touchpad, a stylus, a mouse, or a microphone.

Network system 560 is responsible for communicating information between processing unit 510, memory 520, network interface 530, user output device 540, and user input device 550. Network system 560 may, for example, include a number of different types of busses (e.g., serial and parallel).

In certain modes of operation, computer system 500, according to instructions 522, may analyze the movements of an animal to determine its health status. For example, the computer system may determine the amount of time that an animal spends at a water trough. In the time between visits to the trough may be evaluated in combination with the length of the visits to make a health diagnosis for the animal.

Processing 510 unit may implement any of the other procedures discussed herein, to accomplish these operations.

Computer system 500 provides a variety of features. For example, the system may regulate the distribution of water in an animal watering system to maintain an appropriate amount of water with appropriate properties. Additionally, the computer system may adjust properties of water when an animal approaches. Thus, the computer system may provide a treatment style protocol that matches water to animals. Furthermore, the computer system may compile data from an animal watering system and from each animal being monitored. System 500 can make proper decisions twenty-four hours a day based on the program determined by the operator of the system. Custom features can be changed based on geographical location, type of operation, and type of animal and breed.

Figure 6:
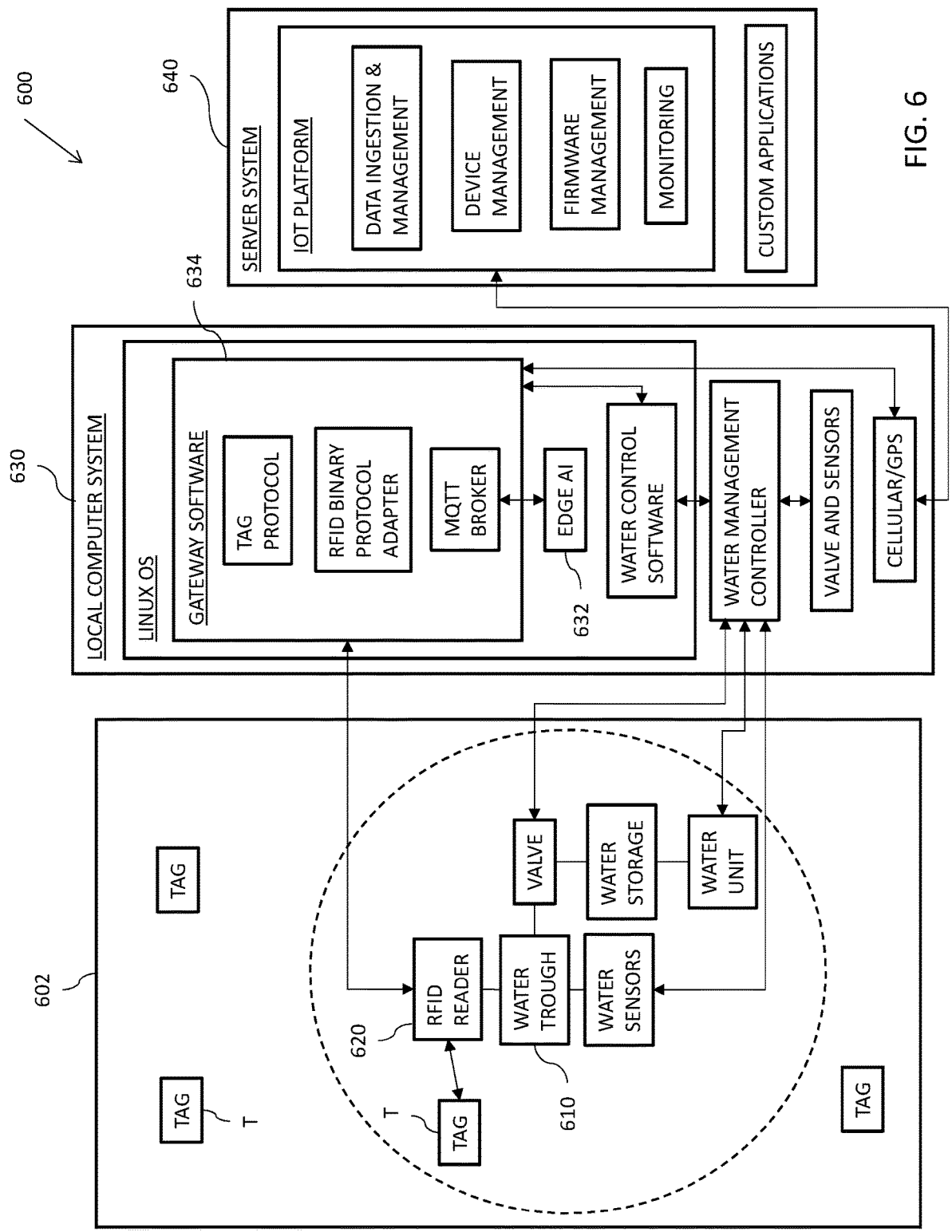
FIG. 6 is a block diagram illustrating an example system architecture for an aspect of a food supply tracking, verification, and feedback system.

FIG. 6 is a block diagram illustrating an example system architecture for an aspect of a food supply tracking, verification, and feedback system 600. System 600 may, for example, be used at a ranch or a feedlot. In general, system 600 is an RFID-based system that tracks an animal's approaches to and dwell times at a water trough 610.

Similar to system 100, system 600 uses tags T on animals, which are located in an enclosure 602 (e.g., a pen or pasture). As the animals move around the enclosure, their associated tags come into range of the RFID reader 620, which is co-located with water trough 610. Thus, the general movements of the animals around the pen, as well as their actual approach to water, may be determined. In particular implementations, multiple RFID readers may be used—one with a longer ranger (e.g., 10 m) and one with a shorter range (e.g., 1 m). The tags T may, for example, generate power assisted responses.

When an animal approaches water trough 610, its tag T may be read and reported to a local computer system 630, which together with RFID reader 620 may compose part of a tag reader system. The local computer system may determine the identity of the animal, store the approach, and determine whether additional water should be released into the trough (e.g., to adjust ORP). Additionally, assuming fine enough granularity, the dwell time of the animal at the water trough may be determined, which may be used as an approximation for water consumption.

The local components of system 600 (e.g., RFID reader 620, valve 611, water unit 614, and local computer system 630) may be communicatively coupled to each other through wireline and/or wireless techniques. Wireline may include co-axial cable, twisted-pair wire, or any other appropriate coupling. Wireline communication may, for example, be accomplished with Power of Ethernet or Ethernet over Power. Wireless communication techniques may include WiFi, Bluetooth™, Near Field Communication (NFC), radio-frequency identification (RFID), or Zig Bee.

Local computer system 630 may, for example, be implemented on a circuit board and may include one or more processors and memory. Local computer system 630 may assess animal health and control water. System 630 may, for example, use a machine learning module to make quick decisions regarding animals as they approach. For example, the system may take into account the animal's temperature, breed, drinking habits (e.g., frequency of visits and dwell time), and herd data to determine if the animal is having a health issue. The system may, for instance, process the data through a matrix to perform this analysis. The system can also take into account the water properties, as measured by water sensors 612, to determine whether to release treated water into the trough. System 630 may house the various containers needed to maintain the hardware and software associated with the system 600.

As illustrated, system 630 includes an edge intelligence application 632. Edge intelligence application 632 receives the raw data (e.g., tag and water data) from gateway software 634 and analyzes the data to determine if any action regarding an animal needs to be taken. For example, this includes determining if the animal is suspect or sick. If the edge intelligence application determines, for instance, that an animal is in need of ionized water—based on movement criteria from the rules engine application—it sends commands to the gateway software 634 to release ionized water to water trough 610. Edge intelligence application 632 also determines which datapoints are necessary to direct to remote storage systems. Edge computer system may also generate commands for tags (e.g., to illuminate) and for the water treatment unit 614 (e.g., to power up and/or power down).

In particular implementations, edge intelligence application 632 contains neural network, tensor, and mathematical software that is used to take inputs and produce outputs that are based on the aggregate weighting of the neural network, tensor, and mathematical software. This software is used to make decisions on how to operate the rest of the system (e.g., water and tags) without having to ask a remote server system for information.

Periodically, the movement data and the water consumption data for the animal may be uploaded to a server system 640, which may, for example, be cloud-based. The server system may provide a centralized repository for data regarding each animal in a food supply tracking, verification, and feedback system. In particular implementations, server system 640 may monitor the health status of the animal (e.g., based on its movements and/or water consumption). If an animal appears to be at risk, server system 640 may generate an alert (e.g., to be posted on a user device). Server system 640 may also collect data from other points in a food supply tracking, verification, and feedback system (e.g., at a packer, a distributor, and/or a retailer).

Figure 7:
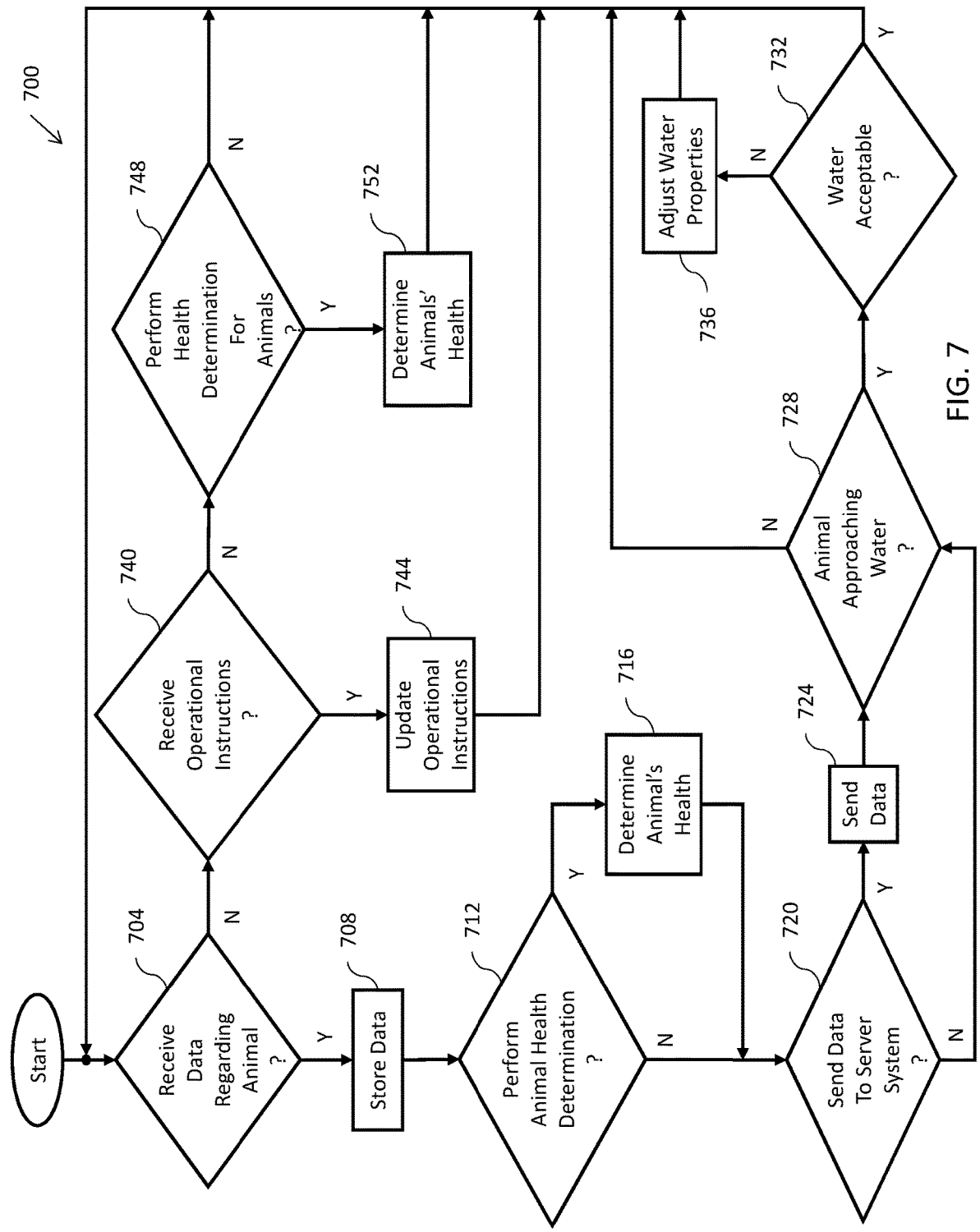
FIG. 7 is a flowchart illustrating example operations of a process for food supply tracking, verification, and feedback.

FIG. 7 illustrates an example process 700 for food supply tracking, verification, and feedback. Process 700 may, for example, be performed by a tag reader system such as tag reader system 122.

Among other things, process 700 calls for determining whether data regarding an animal has been received (operation 704). Data may, for example, be received by sensing a tag attached to an animal (e.g., an RFID tag attached to the animal). The mere fact that the tag has been sensed may provide a variety of information (e.g., the animal is moving, the animal is not moving, the animal is approaching water, the animal is dwelling at water, the animal is approaching food, the animal is exiting/entering a certain type of pen, etc.). Additionally, in some implementations, data may be read from the tag. For example, data such as temperature and movement may be recorded by the tag and transferred once the tag is in sensing range. In certain implementations, data may be received from a remote computer system (e.g., a server system), which may include raw data or an analysis (e.g., a health classification). If data is received for the animal, process 700 calls for storing the data (operation 708). The data may, for example, be stored in a local database, from which it may or may not be transferred to a remote database at a future time.

Process 700 also calls for determine whether to perform an animal health determination (operation 712). Determining whether to perform an animal health determination may, for example, be based on how long it has been since data has been received regarding the animal, how long it has been since a health determination was performed for the animal, or if a certain type of data is received (e.g., elevated temperature). If an animal health determination should be performed, process 700 calls for performing a health determination for the animal (operation 716). An animal health determination may, for example, be accomplish by analyzing one or more factors (e.g., general movement, visits to water troughs, visits to food, temperature, etc.). The available factors may be analyzed using tensor, neural network, and mathematical software, and a health determination (e.g., well, potentially sick, or sick) may be made.

Process 700 further calls for determining whether to send data to a server system (operation 720). This determination may be made based on the type of data received and/or the health determination. For example, data providing health indications of the animal (e.g., general movements, visits to water, visits to food, etc.) may be sent while general diagnostic information may be stored locally or sent at a later time. As another example, if an animal's health status has not changed, the data may not be sent, at least not right away. If data should be sent to a server system, the data is sent (operation 724).

Process 700 further calls for determining whether an animal is approaching water (operation 728). This determination may, for example, be made by determining that the animal is within range of a sensor (e.g., an RFID reader) located near the water. If the animal is approaching water, process 700 calls for determining whether the water is acceptable (operation 732). Determining whether the water is acceptable may, for example, include determining the current properties of the water (e.g., pH, ORP, temperature, etc.), which could be done by reading sensors, and the health condition of the animal. For example, if the animal is healthy, a first water ORP (e.g., −200 mV) may be sufficient, and if the animal is sick, a lower water ORP (e.g., −800 mV) may be desired.

If the water is not acceptable, process 700 calls for adjusting one or more properties of the water (operation 736). Adjusting the water properties may, for example, be accomplished by releasing previously stored water into the trough and/or activating a water treatment unit. This may adjust the water's ORP and/or pH.

Returning to operation 704, if no data has been received regarding an animal, process 700 calls for determining whether operational instructions (e.g., software) have been received (operation 740). Operational instructions may, for example, alter the way in which the health determination is performed, the data conveyed to the server system, the acceptable water properties for an animal, and/or the physical operation of the tag reader system. In regards to the operation of the tag reader system, the operational instructions may, for example, adjust read timings, antenna output power, and maintenance windows. If operational instructions have been received, process 700 calls for updating the operational instructions (operation 744). The operational instructions may, for example, may updated by performing an upgrade on the instructions (e.g., in RAM or ROM).

Process 700 also calls for determining whether to perform a health determination for animals (operation 748). Typically, multiple measurements are required for making a determination regarding an animal's health. For example, if the determination is made based on general movement or repeated visits to a site (e.g., a water trough), the determination need only be made on a somewhat periodic basis (e.g., twice a day or daily). Thus, this determination is typically time driven. However, it can also be event driven. If the animals' health should be determined, process 700 calls for determining the animals' health. An animal health determination may, for example, be accomplish by analyzing one or more factors (e.g., general movement, visits to water troughs, visits to food, temperature, etc.). The available factors may be analyzed using tensor, neural network, and mathematical software, and a health determination (e.g., well, potentially sick, or sick) may be made.

Although FIG. 7 illustrates an example process for food supply tracking, verification, and feedback, other processes for food supply tracking, verification, and feedback may include fewer, additional, and/or a different arrangement of operations. For example, a process may not call for performing an animal health determination after receiving data regarding an animal. Instead, for example, the health determination may be made on a periodic basis or received from a remote location. As another example, a process may not call for determining whether to send data to a server system. Instead, for example, the data may be stored locally or sent to the server system without regard to its type. As another example, a process may not call for determining whether the animal is approaching water and adjusting the water properties.

Figure 8:
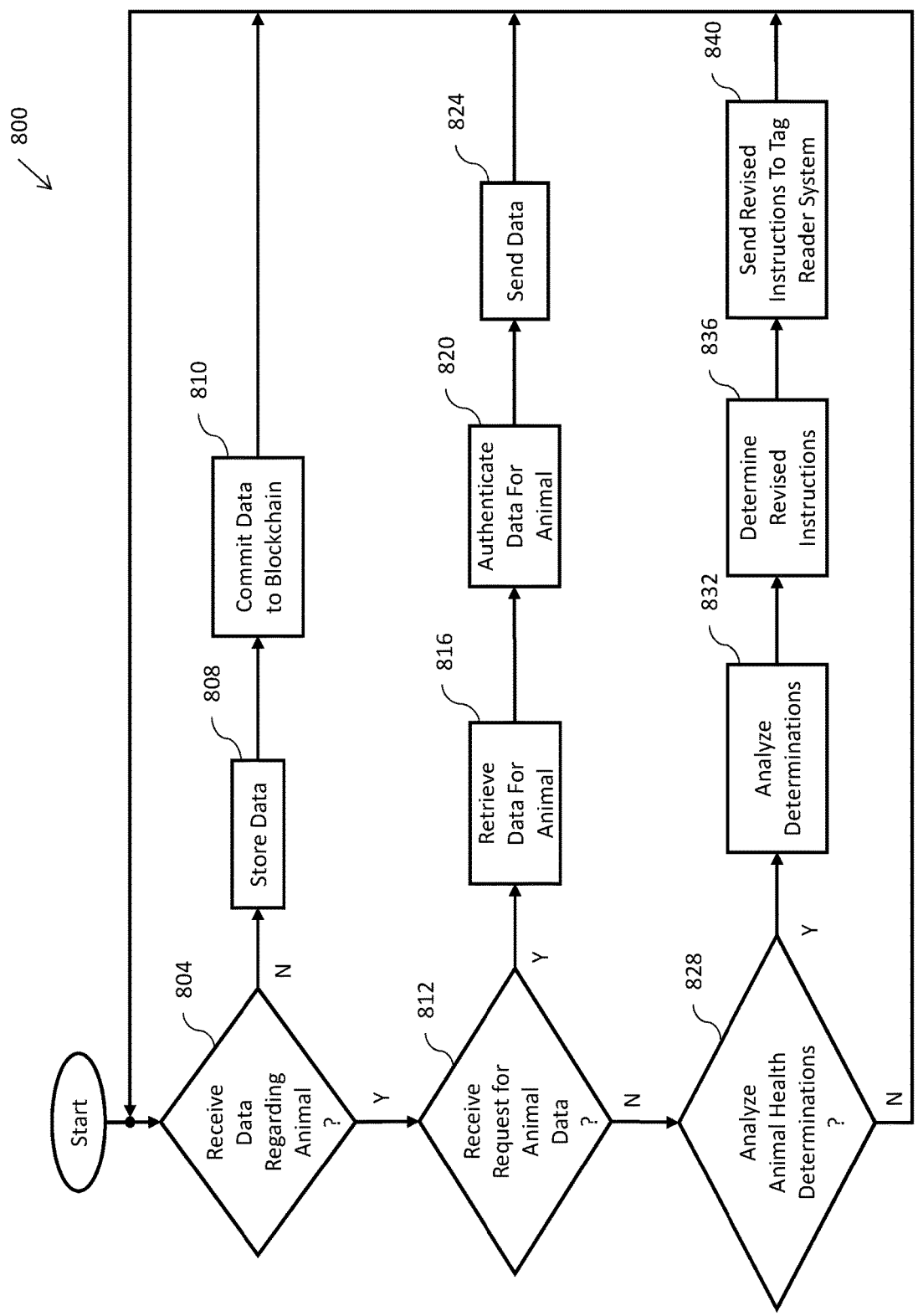
FIG. 8 is a flowchart illustrating example operations of a process for food supply tracking, verification, and feedback.

FIG. 8 illustrates an example process 800 for food supply tracking, verification, and feedback. Process 800 may, for example, be performed by a server system such as server system 180.

Among other things, process 800 calls for determining whether data regarding an animal has been received (operation 804). The data may, for example, include raw data or processed data. Raw data may, for example, include animal movements or lack thereof, animal approaches to water, animal dwells at water, animal approaches to food, animal entrances/exits to/from a certain pen, and animal temperature. Processed data may, for example, include animal health classification. If data is received for an animal, process 800 calls for storing the data (operation 808). The data may, for example, be stored in a local database. Process 800 also calls for committing the data to a blockchain (operation 810). Committing the data to a blockchain may, for example, include placing the data, either alone or in combination with other animal data, in a body of a block and then cryptographically hashing the data. A hash of the cryptographic hash of the data, along with other data, may be stored in the subsequent block in the chain. Placing the data in a blockchain may provide one manner of authenticating it by verifying that it is accurate (e.g., has not been tampered with).

Process 800 additionally calls for determining whether a request for data regarding an animal has been received (operation 812). The request may, for example, originate from a remote computer system (e.g., of a consumer or a retailer). A request typically includes an identifier associated with the animal. The identifier may, for example, come from a barcode. If a request for data regarding an animal has been received, process calls for retrieving data regarding the animal (operation 816) and authenticating at least part of the data (operation 820). Authenticating the data may, for example, include making sure that the data is consistent with data in a blockchain and consistent with reported animal health. For instance, if an animal has been designated as never receiving antibiotics, the animal's health history may be reviewed to determine if the animal was ever sick or ever in a hospital pen. Process 800 also calls for sending the data to the device (operation 824).

Process 800 further calls for determining whether to analyze animal health determinations (operation 828). Analyzing animal health determination may, for example, be performed on a time basis (e.g., weekly or monthly) or an event basis (e.g., on the outbreak of a large number of sick animals).

If animal health determinations should be analyzed, process 800 calls for analyzing the health determinations (operation 832). Analyzing animal health determinations may, for example, be accomplished by apply machine learning to animal health data and animal health diagnoses. Example animal health data can include animal movement, lack of animal movement, visits to water troughs, dwell times at water troughs, visits to food troughs, and animal temperature. Animal health diagnoses may be performed by a veterinarian or other trained animal caretaker. Animal temperature may be used as a diagnostic tool for determining animal health. In general, by correlating the animal health data with animal health diagnoses, tensors can be built to provide future diagnoses of animals based on one or more health criteria. Moreover, the health diagnoses can be varied depending on type of animal (e.g., cow versus horse versus sheep) and breed of animal (e.g., brahma versus angus versus hereford). With sufficient data, adjustments in the health classifications may be used to accommodate a large number of variables.

Particular implementations may also factor in weather and region. For example, it may be known that animals are more susceptible to becoming sick when it is cold, raining, and/or hot. Additionally, animal health conditions may vary by region (e.g., low altitude versus high altitude, dry versus wet, and/or hot versus cold). For instance, cattle in the southern regions of the United States need to be hydrated more frequently than cattle in the northern regions. Thus, the correlations between animal health data and animal health diagnoses may be different based on the weather and region.

Process 800 also calls for determining revised instructions for a tag reader system (operation 836). These revised instructions are based on the revised animal health determinations. The instructions may take the form of actual software code or animal health evaluation data (e.g., factor weighting). Process 800 also calls for sending the revised instructions to the tag reader system (operation 840), at which the instructions may be implemented.

Although FIG. 8 illustrates an example process for food supply tracking, verification, and feedback, other processes for food supply tracking, verification, and feedback may include fewer, additional, and/or a different arrangement of operations. For example, a process may include performing an animal health determination. An animal health determination may, for example, be accomplish by analyzing one or more factors (e.g., general movement, visits to water troughs, visits to food, temperature, etc.). The available factors may be analyzed using tensor, neural network, and mathematical software, and a health determination (e.g., well, potentially sick, or sick) may be made. The animal health determination may then be sent to a remote computer system (e.g., a tag reader system). As another example, a process may include analyzing water properties (e.g., pH, ORP, temperature, etc.). For instance, the health achieved for animals with certain water properties could be analyzed using machine learning in an attempt to optimize the water properties. The water properties could, for example, be established for different classifications of animals (e.g., well, potentially sick, and sick). Moreover, the water properties could be varied depending on type of animal (e.g., cow versus horse versus sheep) and breed of animal (e.g., brahma versus angus versus hereford). Additionally, the water properties may be different depending on the weather (e.g., cold, hot, rainy, snowy, etc.) are region (e.g., low altitude versus high altitude, dry versus wet, and/or hot versus cold). With sufficient data, adjustments in the water properties may be used to accommodate a large number of variables.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modification and variations will be apparent to those of ordinary skill in the art without departing from the scope and spirit of the disclosure. The implementations were chosen and described in order to explain the principles of the disclosure and the practical application and to enable others or ordinary skill in the art to understand the disclosure for various implementations with various modifications as are suited to the particular use contemplated.

A number of implementations have been described for food supply tracking, verification, and feedback, and several others have been mentioned or suggested. Moreover, those skilled in the art will readily recognize that a variety of additions, deletions, modifications, and substitutions may be made to these implementations while still achieving food supply tracking, verification, and feedback. Thus, the scope of the protected subject matter should be judged based on the following claims, which may capture one or more concepts of one or more implementations.

The invention claimed is:

1. A food supply tracking, authentication, and feedback system, the system comprising:
an electronic tag configured to be coupled to an animal;
a first electronic tag reader system associated with an entity at which the animal is raised, the first electronic tag reader system adapted to sense the electronic tag and obtain animal data due to the sensing of the electronic tag;
a second electronic tag reader system associated with an entity that processes the animal into meat packages, the second electronic tag reader system adapted to sense the electronic tag and associate at least one code for the meat packages with the animal;
a server system that receives and stores data regarding the raising and processing of the animal, the server system configured to receive the code and provide authenticated data regarding the animal; and
a code reader system associated with a retailer that offers the meat packages to consumers, the code reader system adapted to sense the code, send it to the server system, and receive data regarding the animal;
wherein the server system analyzes the data regarding the raising and processing of multiple animals, revises instructions for the first electronic tag reader system based on the animal analysis, and sends the revised instructions to the first electronic tag reader system; and
the first electronic tag reader system receives and implements the revised instructions to alter its operations, the first electronic tag reader system altering the health classification of an animal based on the revised instructions from the server system.

2. The food supply system of claim 1, wherein the electronic tag has a unique identifier that is associated with the animal by the server system.

3. The food supply system of claim 1, wherein the electronic tag facilitates monitoring the movements of the animal, and the server system is configured to determine the animal's health status based on the movements.

4. The food supply system of claim 1, wherein the server system is configured to receive, store, and provide data regarding the hydration regimen for the animal, and the server system is configured to determine the animal's health status based on the hydration regimen.

5. The food supply system of claim 4, wherein the hydration regimen data include hydration frequency and antioxidant water consumption.

6. The food supply system of claim 1, wherein the server system stores data regarding the health status of the animal over its life and its inoculation history.

7. The food supply system of claim 1, wherein the first electronic tag reader system alters the water composition for an animal based on the revised instructions from the server system.

8. The food supply system of claim 1, further comprising a code reader system associated with a consumer that purchases meat packages, the code reader system adapted to sense the code, send it to the server system, and receive data regarding the animal.

9. A food supply tracking, authentication, and feedback system, the system comprising:
an electronic tag configured to be coupled to an animal;
an electronic tag reader system associated with an entity at which the animal is raised, the electronic tag reader system adapted to sense the electronic tag and obtain animal data due to the sensing of the electronic tag; and
a server system that receives and stores data regarding the raising of the animal, the server system configured to analyze the data regarding the raising of multiple animals, revise instructions for the electronic tag reader system based on the animal analysis, and send the revised instructions to the electronic tag reader system;

wherein the electronic tag reader system receives and implements the revised instructions to alter its operations, the electronic tag reader system altering the health classification of an animal based on the revised instructions from the server system.

10. The food supply system of claim 9, wherein the electronic tag has a unique identifier that is associated with the animal by the server system.

11. The food supply system of claim 9, wherein the electronic tag facilitates monitoring the movements of the animal, and the server system is configured to determine the animal's health status based on the movements.

12. The food supply system of claim 9, wherein the server system is configured to receive, store, and provide data regarding the hydration regimen for the animal, and the server system is configured to determine the animal's health status based on the hydration regimen.

13. The food supply system of claim 12, wherein the hydration regimen data include hydration frequency and antioxidant water consumption.

14. The food supply system of claim 9, wherein the server system stores data regarding the health status of the animal over its life and its inoculation history.

15. The food supply system of claim 9, wherein the electronic tag reader system includes a water trough and a water control system, the electronic tag reader system being configured to alter the properties of water provided for an animal based on the revised instructions from the server system.

16. The food supply system of claim 9, further comprising a second electronic tag reader system associated with an entity that processes the animal into separate meat packages, the second tag reader system adapted to sense the electronic tag and associate at least one code for the meat packages with the animal.

17. The food supply system of claim 16, further comprising a computer system associated with a retailer that offers the meat packages to consumers, the computer system adapted to sense the code, send it to the server system, and receive data regarding the animal.

18. The food supply system of claim 16, further comprising a computer system associated with a consumer that purchases meat packages, the computer system adapted to sense the code, send it to the server system, and receive data regarding the animal.

19. The food supply system of claim 16, wherein the server system is configured to receive the code and provide authenticated data regarding the animal.

* * * * *